(12) United States Patent
Cook et al.

(10) Patent No.: US 11,560,311 B2
(45) Date of Patent: Jan. 24, 2023

(54) APPARATUS FOR THERMALLY CRACKING A HYDROCARBON GAS

(71) Applicant: LytEn, Inc., San Jose, CA (US)

(72) Inventors: Daniel Cook, Woodside, CA (US); Hossein-Ali Ghezelbash, Santa Clara, CA (US); Bryce H. Anzelmo, Mountain View, CA (US); David Tanner, Yuba City, CA (US); Shreeyukta Singh, San Jose, CA (US)

(73) Assignee: Lyten, Inc., San Jose, CA (US)

( * ) Notice: Subject to any disclaimer, the term of this patent is extended or adjusted under 35 U.S.C. 154(b) by 44 days.

(21) Appl. No.: 17/338,282

(22) Filed: Jun. 3, 2021

(65) Prior Publication Data

US 2021/0292170 A1    Sep. 23, 2021

Related U.S. Application Data

(63) Continuation of application No. 16/164,077, filed on Oct. 18, 2018, now Pat. No. 11,053,121, which is a
(Continued)

(51) Int. Cl.
| | |
|---|---|
| *C01B 32/152* | (2017.01) |
| *C08J 5/00* | (2006.01) |
| *C22C 1/05* | (2006.01) |
| *B82Y 40/00* | (2011.01) |
| *B82Y 30/00* | (2011.01) |
| *G01N 21/65* | (2006.01) |
| *C01B 32/158* | (2017.01) |
| *C01B 32/20* | (2017.01) |
| *C01B 32/225* | (2017.01) |
| *C01B 32/184* | (2017.01) |

(Continued)

(52) U.S. Cl.
CPC .......... *C01B 32/152* (2017.08); *B22F 1/0547* (2022.01); *B82Y 30/00* (2013.01); *B82Y 40/00* (2013.01); *C01B 32/158* (2017.08); *C01B 32/182* (2017.08); *C01B 32/184* (2017.08); *C01B 32/20* (2017.08); *C01B 32/225* (2017.08); *C08J 5/005* (2013.01); *C22C 1/058* (2013.01); *G01N 21/65* (2013.01); *C07C 2604/00* (2017.05)

(58) Field of Classification Search
CPC ... C01B 32/152; C01B 32/158; C01B 32/182; C01B 32/184; C01B 32/20; C01B 32/225; B22F 1/0547; B82Y 30/00; B82Y 40/00; C08J 5/005; C22C 1/058; G01N 21/65; C07C 2604/00
See application file for complete search history.

(56) References Cited

U.S. PATENT DOCUMENTS

| | | | |
|---|---|---|---|
| 5,876,684 A * | 3/1999 | Withers | C30B 29/02 204/173 |
| 2014/0120723 A1 * | 5/2014 | Fu | C23C 16/14 438/680 |

* cited by examiner

*Primary Examiner* — Daniel C. McCracken
(74) *Attorney, Agent, or Firm* — Paradice & Li LLP

(57) ABSTRACT

A nanoparticle or agglomerate which contains connected multi-walled spherical fullerenes coated in layers of graphite. In different embodiments, the nanoparticles and agglomerates have different combinations of: a high mass fraction compared to other carbon allotropes present, a low concentration of defects, a low concentration of elemental impurities, a high Brunauer, Emmett and Teller (BET) specific surface area, and/or a high electrical conductivity. Methods are provided to produce the nanoparticles and agglomerates at a high production rate without using catalysts.

19 Claims, 11 Drawing Sheets

Related U.S. Application Data continuation of application No. 15/794,965, filed on Oct. 26, 2017, now Pat. No. 10,112,837, which is a continuation of application No. 15/594,032, filed on May 12, 2017, now Pat. No. 9,862,606, which is a continuation-in-part of application No. 15/470,450, filed on Mar. 27, 2017, now Pat. No. 9,862,602.

(51) Int. Cl.
*B22F 1/054* (2022.01)
*C01B 32/182* (2017.01)

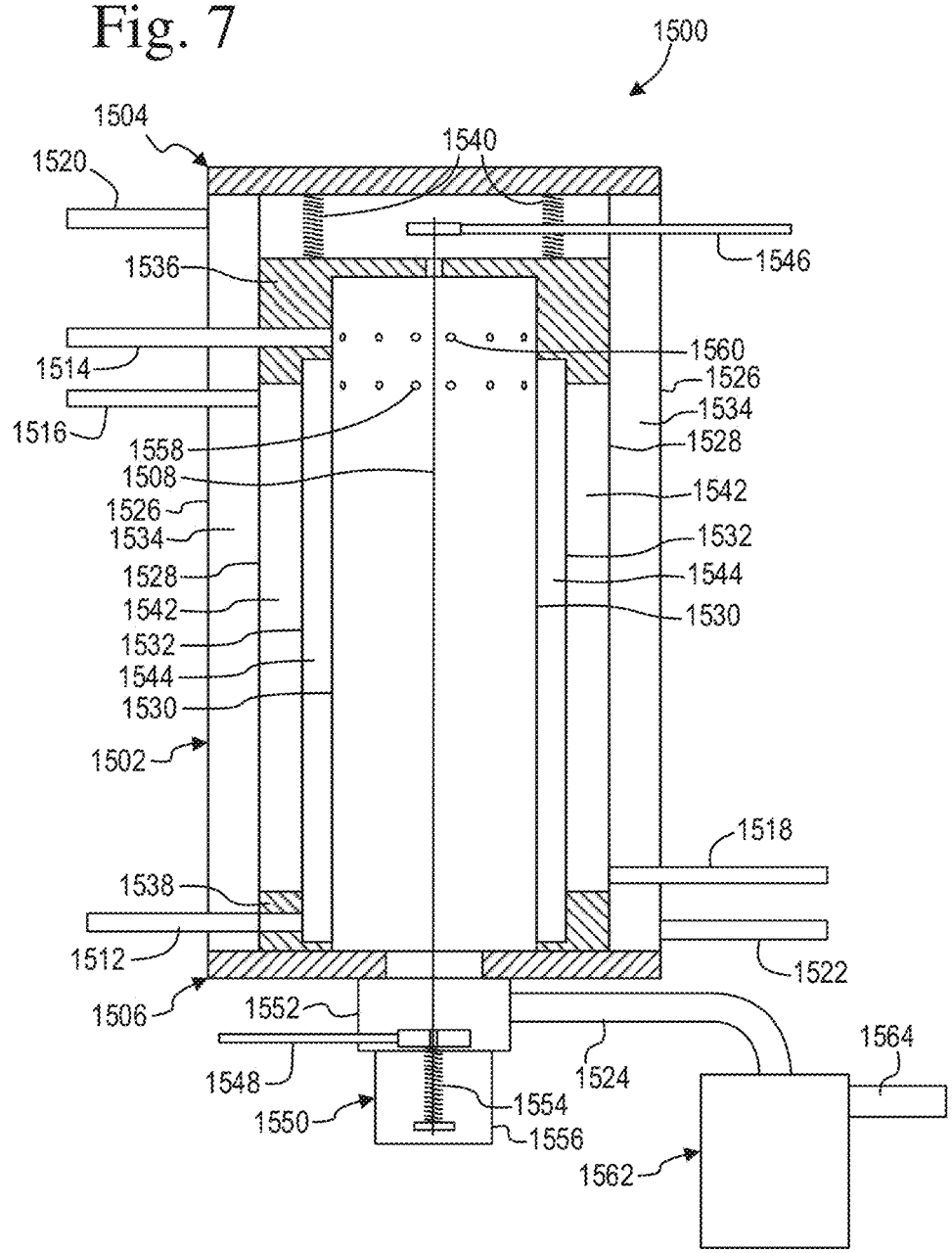

APPARATUS FOR THERMALLY CRACKING A HYDROCARBON GAS

CROSS-REFERENCE TO RELATED APPLICATIONS

This patent application is a continuation application and claims priority to U.S. patent application Ser. No. 16/164,077 filed Oct. 18, 2018, which is a continuation of U.S. patent application Ser. No. 15/794,965 filed Oct. 26, 2017, which is a continuation of U.S. patent application Ser. No. 15/594,032 filed May 12, 2017, which is a continuation-in-part of U.S. patent application Ser. No. 15/470,450 filed Mar. 27, 2017, all of which are assigned to the assignee hereof. The disclosures of all prior Applications are incorporated by reference in this Patent Application.

BACKGROUND

Various crude or refined hydrocarbons (e.g., methane, ethane, propane, etc.) can be pyrolized or cracked to synthesize hydrogen and to produce higher-order carbon substances (e.g., graphene and fullerenes). However, some of the processes used to produce these higher-order carbon substances require the use of catalysts, such as metal catalysts. Additionally, some processes result in the presence of impurities within the higher-order carbon substances. Furthermore, some processes require the formation of a "seed" or "core" around which the higher-order carbon substances are formed.

Different allotropes of carbon can be generated by cracking hydrocarbons utilizing thermal processes. One example of a process for generating lower-order carbon substances (e.g., carbon black) is the solar thermolysis of methane (both with and without a catalyst) to produce hydrogen and carbon black. An example of a process for generating higher-order carbon substances is the catalytic decomposition of methane in a quartz tubular reactor to produce hydrogen and highly graphitic carbon nanotubes, microfibers, microballs, and carbon onions.

FIG. 1A shows a schematic of graphite, where carbon forms multiple layers of a two-dimensional, atomic-scale, hexagonal lattice in which one atom forms each vertex. Graphene is a single layer of graphite. FIG. 1B shows a schematic of a carbon nanotube, where carbon atoms form a hexagonal lattice that is curved into a cylinder. Carbon nanotubes can also be referred to as cylindrical fullerenes. FIG. 1C shows a schematic of a C60 buckminsterfullerene, where a single layer of a hexagonal lattice of carbon atoms forms a sphere. Other spherical fullerenes exist that contain single layers of hexagonal lattices of carbon atoms, and can contain 60 atoms, 70 atoms, or more than 70 atoms. FIG. 1D shows a schematic of a carbon nano-onion from U.S. Pat. No. 6,599,492, which contains multiple concentric layers of spherical fullerenes.

SUMMARY

In some embodiments, a carbon nanoparticle comprises at least two connected multi-walled spherical fullerenes, and layers of graphene coating the connected multi-walled spherical fullerenes. In some embodiments, a Raman spectrum of the carbon nanoparticle using 532 nm incident light has a first Raman peak at approximately 1350 $cm^{-1}$ and a second Raman peak at approximately 1580 $cm^{-1}$, and a ratio of an intensity of the first Raman peak to an intensity of the second Raman peak is from 0.9 to 1.1. In some embodiments, a ratio of graphene to multi-walled spherical fullerenes is from 10% to 80%.

In some embodiments, the carbon nanoparticle described above contains multi-walled spherical fullerenes that do not comprise a seed particle or a void at the center of the multi-walled spherical fullerenes. In some embodiments, the carbon nanoparticle described above contains multi-walled spherical fullerenes that have an average diameter from 50 nm to 500 nm.

In some embodiments, a carbon aggregate comprises a plurality of the carbon nanoparticles described above, wherein a diameter across the carbon aggregate is from 10 microns to 500 microns. In some embodiments the carbon aggregate has a ratio of graphene to multi-walled spherical fullerenes from 10% to 80%. In some embodiments, the carbon aggregate has a ratio of carbon to other elements, except H, in the carbon aggregate is greater than 99.9%. In some embodiments, the carbon aggregate has a Brunauer, Emmett and Teller (BET) specific surface area of the carbon aggregate is from 10 $m^2/g$ to 200 $m^2/g$. In some embodiments, a plurality of the carbon aggregates are compressed into a pellet, and the pellet has an electrical conductivity from 500 S/m to 20000 S/m.

In some embodiments, a mixture comprises a liquid and a plurality of the carbon nanoparticles described above. In some embodiments, a conductive ink comprises a plurality of the carbon nanoparticles described above.

In some embodiments a method comprises flowing a hydrocarbon feedstock process gas into a reaction zone, thermally cracking molecules of the feedstock process gas in the reaction zone, reacting the thermally cracked molecules to form carbon aggregates, each comprising at least two connected multi-walled spherical fullerenes coated in layers of graphene, and collecting the carbon aggregates. In some embodiments, a Raman spectrum of the carbon aggregates using 532 nm incident light has a first Raman peak at about 1350 cm-1 and a second Raman peak at about 1580 cm-1, and a ratio of an intensity of the first Raman peak to an intensity of the second Raman peak is from 0.9 to 1.1. In some embodiments, the collected carbon aggregates are size-reduced by mechanical means.

In some embodiments, the multi-walled spherical fullerenes produced using the method described above do not comprise a seed particle or a void at the center of the multi-walled spherical fullerenes. In some embodiments, the multi-walled spherical fullerenes produced using the method described above have an average diameter across the carbon aggregates is from 10 microns to 500 microns. In some embodiments, the multi-walled spherical fullerenes produced using the method described above have an average diameter from 50 nm to 500 nm. In some embodiments, the multi-walled spherical fullerenes produced using the method described above have a ratio of graphene to multi-walled spherical fullerenes is from 10% to 80%. In some embodiments, the multi-walled spherical fullerenes produced using the method described above have a ratio of carbon to other elements, except H, in the carbon aggregates is greater than 99.9%. In some embodiments, the multi-walled spherical fullerenes produced using the method described above have a Brunauer, Emmett and Teller (BET) specific surface area of the carbon aggregates is from 10 m2/g to 200 m2/g.

In some embodiments, the carbon aggregates are produced by the method described above, and then compressed into a pellet, wherein the pellet has an electrical conductivity from 500 S/m to 20000 S/m. In some embodiments, the carbon aggregates are produced by the method described above, using a gas resonance time of 0.1 seconds to 30 seconds. In some embodiments, the carbon aggregates are produced by the method described above, using a gas flow rate of 1 slm to 10 slm and a production rate from 10 g/hr to 200 g/hr.

In some embodiments, the carbon aggregates are produced by the method described above, and then post-processed using a method selected from group consisting of chemical etching, thermal annealing, particle sintering, spark plasma sintering, steaming, filtering, lypolizing, processing using Hummers' method, doping, and adding elements.

BRIEF DESCRIPTION OF THE DRAWINGS

FIG. 7 depicts a simplified schematic view of a cracking apparatus in accordance with at least some embodiments.

DETAILED DESCRIPTION

The present disclosure relates to carbon nanoparticles and aggregates that include different allotropes of (i.e., various forms of) carbon, including graphene, various fullerenes, and combinations thereof, as described below. In some embodiments, the carbon nanoparticles and aggregates are characterized by a high "uniformity" (i.e., high mass fraction of desired carbon allotropes), high degree of "order" (i.e., low concentration of defects), and/or high "purity" (i.e., low concentration of elemental impurities), in contrast to the lower uniformity, less ordered and lower purity particles achievable with conventional systems and methods. In some embodiments, the carbon nanoparticles and aggregates described herein are characterized by a size that is substantially larger than comparable prior art particles. In some embodiments, the carbon nanoparticles and aggregates described herein are characterized by a well-ordered structure with high purity as illustrated by an idealized carbon nanoparticle 200 shown in FIG. 2. The carbon allotrope in FIG. 2 contains two connected multi-walled spherical fullerenes (MWSFs) 201 and 202 with layers of graphene 203 coating the connected MWSFs 201 and 202). The allotrope shown in FIG. 2 is also core-less (i.e., does not contain a core of a material other than carbon at the center of the spherical fullerene).

Figure 1A:
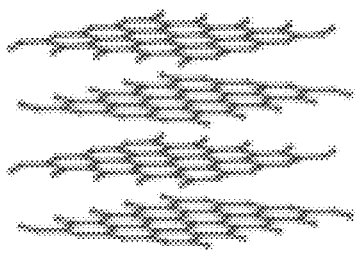
FIGS. 1A-1D are schematics of carbon allotropes from the prior art.
Figure 1B:
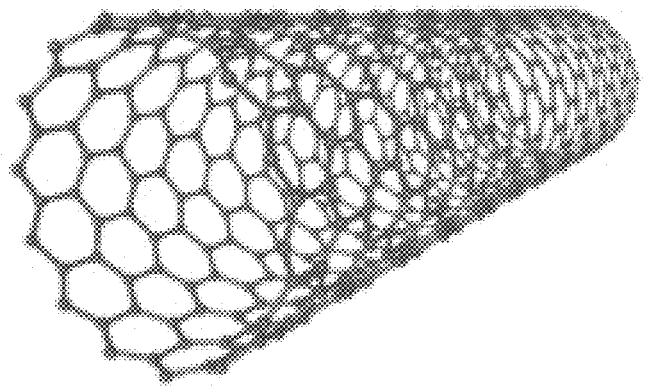
Figure 1C:
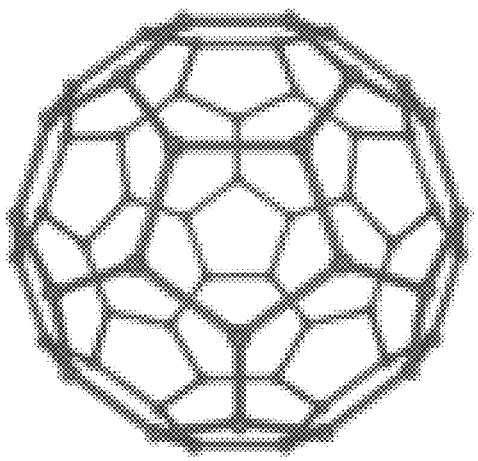
Figure 1D:
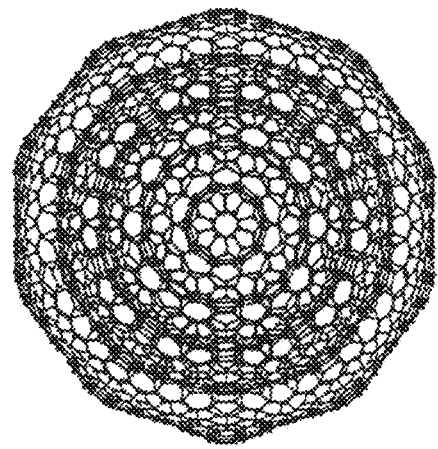
Figure 2:
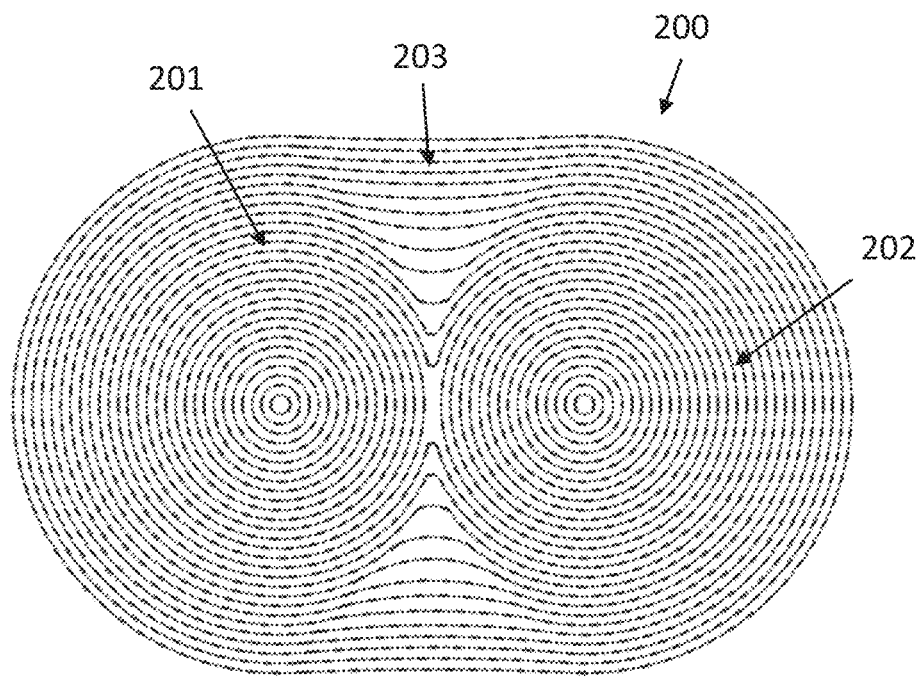
FIG. 2 is a schematic of idealized connected multi-walled spherical fullerenes, in accordance with some embodiments.

The idealized nanoparticle shown in FIG. 2 has high uniformity since the ratio of MWSFs to graphene is high, is well-ordered since there are no point defects (e.g., missing carbon atoms) and no distorted carbon lattices, and has a high purity since there are no elements (e.g., a core of impurities) other than carbon, in contrast with low uniformity mixtures of MWSFs mixed with other carbon allotropes, poorly-ordered MWSFs with many point defects and distorted lattices, and low purity MWSFs (e.g., with seed particles at the core). In other embodiments, the connected MWSFs do contain a core. In some embodiments, the core is a void, a carbon-based material that is not an MWSF (e.g., amorphous carbon), or a seed that is not carbon-based.

In some embodiments, the nanoparticles produced using the methods described herein contain MWSFs or connected MWSFs and have a high uniformity (e.g., a ratio of graphene to MWSF from 20% to 80%), a high degree of order (e.g., a Raman signature with an ID/IG ratio from 0.95 to 1.05), and a high purity (e.g., the ratio of carbon to other elements, other than H, is greater than 99.9%). In some embodiments, the nanoparticles produced using the methods described herein contain MWSFs or connected MWSFs, and the MWSFs do not contain a core composed of impurity elements other than carbon. In some cases, the particles produced using the methods described herein are aggregates containing the nanoparticles described above with large diameters (e.g., greater than 10 microns across).

Conventional methods have been used to produce particles containing multi-walled spherical fullerenes (MWSFs) with a high degree of order, but the conventional methods lead to carbon products with a variety of shortcomings. For example, high temperature synthesis techniques lead to particles with a mixture of many carbon allotropes and therefore low uniformity (e.g., less than 20% fullerenes to other carbon allotropes) and/or small particle sizes (e.g., less than 1 micron, or less than 100 nm in some cases). Methods utilizing catalysts lead to products including the catalyst elements and therefore have low purity (e.g., less than 95% carbon to other elements). These undesirable properties also often lead to undesirable electrical properties of the resulting carbon particles (e.g., electrical conductivity less than 1000 S/m).

In some embodiments, the carbon nanoparticles and aggregates described herein are characterized by Raman spectroscopy that is indicative of the high degree of order, and the uniformity of the structure. In some embodiments, the uniform, ordered and/or pure carbon nanoparticles and aggregates described herein are produced using relatively high speed, low cost improved thermal reactors and methods, as described below. Additional advantages and/or improvements will also become apparent from the following disclosure.

In the present disclosure, the term "graphene" refers to an allotrope of carbon in the form of a two-dimensional, atomic-scale, hexagonal lattice in which one atom forms each vertex. The carbon atoms in graphene are sp2-bonded. Additionally, graphene has a Raman spectrum with two main peaks: a G-mode at approximately 1580 cm$^{-1}$ and a D-mode at approximately 1350 cm$^{-1}$ (when using a 532 nm excitation laser). In the present disclosure, the term "fullerene" refers to a molecule of carbon in the form of a hollow sphere, ellipsoid, tube, or other shapes. Spherical fullerenes can also be referred to as Buckminsterfullerenes, or bucky balls. Cylindrical fullerenes can also be referred to as carbon nanotubes. Fullerenes are similar in structure to graphite, which is composed of stacked graphene sheets of linked hexagonal rings.

Fullerenes may also contain pentagonal (or sometimes heptagonal) rings.

In the present disclosure, the term "multi-walled fullerene" refers to fullerenes with multiple concentric layers. For example, multi-walled nanotubes (MWNTs) contain multiple rolled layers (concentric tubes) of graphene. Multi-walled spherical fullerenes (MWSFs) contain multiple concentric spheres of fullerenes.

In the present disclosure, the term "nanoparticle" refers to a particle that has a size from 1 nm to 900 nm. The nanoparticle can include one or more type of structure (e.g., crystal structure, defect concentration, etc.), and one or more type of atom. The nanoparticle can be any shape, including but not limited to spherical shapes, spheroidal shapes, dumbbell shapes, cylindrical shapes, elongated cylindrical type shapes, rectangular prism shapes, disk shapes, wire shapes, irregular shapes, dense shapes (i.e., with few voids), porous shapes (i.e., with many voids), etc.

In the present disclosure, the term "aggregate" refers to a plurality of nanoparticles that are connected together by Van der Waals forces, by covalent bonds, by ionic bonds, by metallic bonds, or by other physical or chemical interactions. Aggregates can vary in size considerably, but in general are larger than about 500 nm.

In some embodiments, a carbon nanoparticle, as described herein, includes two or more connected multi-walled spherical fullerenes (MWSFs) and layers of graphene coating the connected MWSFs. In some embodiments, a carbon nanoparticle, as described herein, includes two or more connected multi-walled spherical fullerenes (MWSFs) and layers of graphene coating the connected MWSFs, and the MWSFs do not contain a core composed of impurity elements other than carbon. In some embodiments, a carbon nanoparticle, as described herein, includes two or more connected multi-walled spherical fullerenes (MWSFs) and layers of graphene coating the connected MWSFs, and the MWSFs do not contain a void (i.e., a space with no carbon atoms greater than approximately 0.5 nm, or 1 nm) at the center. In some embodiments, the connected MWSFs are formed of concentric, well-ordered spheres of sp2-hybridized carbon atoms, as contrasted with spheres of poorly-ordered, non-uniform, amorphous carbon particles.

In some embodiments, the nanoparticles containing the connected MWSFs have an average diameter in a range from 5 to 500 nm, or from 5 to 250 nm, or from 5 to 100 nm, or from 5 to 50 nm, or from 10 to 500 nm, or from 10 to 250 nm, or from 10 to 100 nm, or from 10 to 50 nm, or from 40 to 500 nm, or from 40 to 250 nm, or from 40 to 100 nm, or from 50 to 500 nm, or from 50 to 250 nm, or from 50 to 100 nm.

In some embodiments, the carbon nanoparticles described herein form aggregates, wherein many nanoparticles aggregate together to form a larger unit. In some embodiments, a carbon aggregate includes a plurality of carbon nanoparticles. A diameter across the carbon aggregate is in a range from 10 to 500 microns, or from 50 to 500 microns, or from 100 to 500 microns, or from 250 to 500 microns, or from 10 to 250 microns, or from 10 to 100 microns, or from 10 to 50 microns. In some embodiments, the aggregate is formed from a plurality of carbon nanoparticles, as defined above. In some embodiments, aggregates contain connected MWSFs. In some embodiments, the aggregates contain connected MWSFs with high uniformity (e.g., a ratio of graphene to MWSF from 20% to 80%), a high degree of order (e.g., a Raman signature with an ID/IG ratio from 0.95 to 1.05), and a high purity (e.g., greater than 99.9% carbon).

One benefit of producing aggregates of carbon nanoparticles, particularly with diameters in the ranges described above, is that aggregates of particles greater than 10 microns are easier to collect than particles or aggregates of particles that are smaller than 500 nm. The ease of collection reduces the cost of manufacturing equipment used in the production of the carbon nanoparticles and increases the yield of the carbon nanoparticles. Additionally, particles greater than 10 microns in size pose fewer safety concerns compared to the risks of handling smaller nanoparticles, e.g., potential health and safety risks due to inhalation of the smaller nanoparticles. The lower health and safety risks, thus, further reduce the manufacturing cost.

In some embodiments, a carbon nanoparticle has a ratio of graphene to MWSFs from 10% to 90%, or from 10% to 80% or from 10% to 60%, or from 10% to 40%, or from 10% to 20%, or from 20% to 40%, or from 20% to 90%, or from 40% to 90%, or from 60% to 90%, or from 80% to 90%. In some embodiments, a carbon aggregate has a ratio of graphene to MWSFs is from 10% to 90%, or from 10% to 80% or from 10% to 60%, or from 10% to 40%, or from 10% to 20%, or from 20% to 40%, or from 20% to 90%, or from 40% to 90%, or from 60% to 90%, or from 80% to 90%. In some embodiments, a carbon nanoparticle has a ratio of graphene to connected MWSFs from 10% to 90%, or from 10% to 80% or from 10% to 60%, or from 10% to 40%, or from 10% to 20%, or from 20% to 40%, or from 20% to 90%, or from 40% to 90%, or from 60% to 90%, or from 80% to 90%. In some embodiments, a carbon aggregate has a ratio of graphene to connected MWSFs is from 10% to 90%, or from 10% to 80% or from 10% to 60%, or from 10% to 40%, or from 10% to 20%, or from 20% to 40%, or from 20% to 90%, or from 40% to 90%, or from 60% to 90%, or from 80% to 90%.

In some embodiments, Raman spectroscopy is used to characterize carbon allotropes to distinguish their molecular structures. For example, graphene can be characterized using Raman spectroscopy to determine information such as order/disorder, edge and grain boundaries, thickness, number of layers, doping, strain, and thermal conductivity. MWSFs have also been characterized using Raman spectroscopy to determine the degree of order of the MWSFs.

In some embodiments, Raman spectroscopy is used to characterize the structure of MWSFs or connected MWSFs. The main peaks in the Raman spectra are the G-mode and the D-mode. The G-mode is attributed to the vibration of carbon atoms in sp2-hybridized carbon networks, and the D-mode is related to the breathing of hexagonal carbon rings with defects. When using 532 nm incident light, the Raman G-mode is typically at 1582 cm$^{-1}$ for planar graphite, but can be downshifted for MWSFs or connected MWSFs (e.g., to 1565-1580 cm$^{-1}$). The D-mode is observed at approximately 1350 cm$^{-1}$ in the Raman spectra of MWSFs or connected MWSFs. The ratio of the intensities of the D-mode peak to G-mode peak (i.e., the ID/IG) is related to the degree of order of the MWSFs, where a lower ID/IG indicates higher degree of order. An ID/IG near or below 1 indicates a relatively high degree of order, and a ID/IG greater than 1.1 indicates lower degree of order.

In some embodiments, a carbon nanoparticle or a carbon aggregate containing MWSFs or connected MWSFs, as described herein, has a Raman spectrum with a first Raman peak at about 1350 cm$^{-1}$ and a second Raman peak at about 1580 cm$^{-1}$, when using 532 nm incident light. In some embodiments, the ratio of an intensity of the first Raman peak to an intensity of the second Raman peak (i.e., the ID/IG) for the nanoparticles or the aggregates described herein is in a range from 0.95 to 1.05, or from 0.9 to 1.1, or from 0.8 to 1.2, or from 0.9 to 1.2, or from 0.8 to 1.1, or from 0.5 to 1.5, or less than 1.5, or less than 1.2, or less than 1.1, or less than 1, or less than 0.95, or less than 0.9, or less than 0.8.

In some embodiments, a carbon aggregate containing MWSFs or connected MWSFs, as defined above, has high purity. In some embodiments, the carbon aggregate containing MWSFs or connected MWSFs has a ratio of carbon to metals of greater than 99.99%, or greater than 99.95%, or greater than 99.9%, or greater than 99.8%, or greater than 99.5%, or greater than 99%. In some embodiments, the carbon aggregate has a ratio of carbon to other elements of greater than 99.99%, or greater than 99.95%, or greater than 99.9%, or greater than 99.5%, or greater than 99%, or greater than 90%, or greater than 80%, or greater than 70%, or greater than 60%. In some embodiments, the carbon aggregate has a ratio of carbon to other elements, except H, of greater than 99.99%, or greater than 99.95%, or greater than 99.9%, or greater than 99.8%, or greater than 99.5%, or greater than 99%, or greater than 90%, or greater than 80%, or greater than 70%, or greater than 60%.

In some embodiments, a carbon aggregate containing MWSFs or connected MWSFs, as defined above, has high specific surface area. In some embodiments, the carbon aggregate has a Brunauer, Emmett and Teller (BET) specific surface area from 10 to 200 $m^2/g$, or from 10 to 100 $m^2/g$, or from 10 to 50 $m^2/g$, or from 50 to 200 $m^2/g$, or from 50 to 100 $m^2/g$, or from 10 to 1000 $m^2/g$.

In some embodiments, a carbon aggregate containing MWSFs or connected MWSFs, as defined above, has high electrical conductivity. In some embodiments, a carbon aggregate containing MWSFs or connected MWSFs, as defined above, is compressed into a pellet and the pellet has electrical conductivity greater than 500 S/m, or greater than 1000 S/m, or greater than 2000 S/m, or greater than 3000 S/m, or greater than 4000 S/m, or greater than 5000 S/m, or greater than 10000 S/m, or greater than 20000 S/m, or greater than 30000 S/m, or greater than 40000 S/m, or greater than 50000 S/m, or greater than 60000 S/m, or greater than 70000 S/m, or from 500 S/m to 100000 S/m, or from 500 S/m to 1000 S/m, or from 500 S/m to 10000 S/m, or from 500 S/m to 20000 S/m, or from 500 S/m to 100000 S/m, or from 1000 S/m to 10000 S/m, or from 1000 S/m to 20000 S/m, or from 10000 to 100000 S/m, or from 10000 S/m to 80000 S/m, or from 500 S/m to 10000 S/m. In some cases, the density of the pellet is approximately 1 $g/cm^3$, or approximately 1.2 $g/cm^3$, or approximately 1.5 $g/cm^3$, or approximately 2 $g/cm^3$, or approximately 2.2 $g/cm^3$, or approximately 2.5 $g/cm^3$, or approximately 3 $g/cm^3$. Additionally, tests have been performed in which compressed pellets of the carbon aggregate materials have been formed with compressions of 2000 psi and 12000 psi and with annealing temperatures of 800 C and 1000 C. The higher compression and/or the higher annealing temperatures generally resulted in pellets with higher electrical conductivity, including in a range of 12410.0 S/m to 13173.3 S/m.

High Purity Carbon Allotropes Produced Using Thermal Processing Systems

In some embodiments, the carbon nanoparticles and aggregates described herein are produced using thermal reactors and methods, such as any appropriate thermal reactor and/or method described in the aforementioned U.S. patent application Ser. No. 15/470,450, which is assigned to the same assignee as the present application, and which is incorporated herein by reference as if fully set forth herein for all purposes. Additionally, precursors (e.g., including methane, ethane, propane, butane, and natural gas) can be used with the thermal reactors to produce the carbon nanoparticles and the carbon aggregates described herein.

In some embodiments, the carbon nanoparticles and aggregates described herein are produced using the thermal reactors with gas flow rates from 1 slm (standard liter per minute) to 10 slm, or from 0.1 slm to 20 slm, or from 1 slm to 5 slm, or from 5 slm to 10 slm, or greater than 1 slm, or greater than 5 slm. In some embodiments, the carbon nanoparticles and aggregates described herein are produced using the thermal reactors with gas resonance times from 0.1 seconds to 30 seconds, or from 0.1 seconds to 10 seconds, or from 1 seconds to 10 seconds, or from 1 seconds to 5 seconds, from 5 seconds to 10 seconds, or greater than 0.1 seconds, or greater than 1 seconds, or greater than 5 seconds, or less than 30 seconds.

In some embodiments, the carbon nanoparticles and aggregates described herein are produced using the thermal reactors with production rates from 10 g/hr to 200 g/hr, or from 30 g/hr to 200 g/hr, or from 30 g/hr to 100 g/hr, or from 30 g/hr to 60 g/hr, or from 10 g/hr to 100 g/hr, or greater than 10 g/hr, or greater than 30 g/hr, or greater than 100 g/hr.

In some embodiments, thermal reactors (or cracking apparatuses) and methods can be used for refining, pyrolizing, dissociating or cracking feedstock process gases into constituent components to produce the carbon nanoparticles and the carbon aggregates described herein, as well as other solid and/or gaseous products (e.g., hydrogen gas and/or lower order hydrocarbon gases). The feedstock process gases generally include, for example, hydrogen gas (H2), carbon dioxide (CO2), C1-10 hydrocarbons, aromatic hydrocarbons, other hydrocarbon gases, natural gas, methane, ethane, propane, butane, isobutane, saturated/unsaturated hydrocarbon gases, ethene, propene, etc. and mixtures thereof. The carbon nanoparticles and the carbon aggregates can include, for example, multi-walled spherical fullerenes (MWSFs), connected MWSFs, carbon nanospheres, graphene, graphite, highly ordered pyrolytic graphite, single walled nanotubes, multi-walled nanotubes, other solid carbon products, and/or the carbon nanoparticles and the carbon aggregates described herein.

Some embodiments for producing the carbon nanoparticles and the carbon aggregates described herein include thermal cracking methods that use, for example, an elongated longitudinal heating element optionally enclosed within an elongated casing, housing or body of a thermal cracking apparatus. The body generally includes, for example, one or more tubes or other appropriate enclosures made of stainless steel, titanium, graphite, quartz, or the like. In some embodiments, the body of the thermal cracking apparatus is generally cylindrical in shape with a central elongate longitudinal axis arranged vertically and a feedstock process gas inlet at or near a top of the body. The feedstock process gas flows longitudinally down through the body or a portion thereof. In the vertical configuration, both gas flow and gravity assist in the removal of the solid products from the body of the thermal cracking apparatus.

The heating element generally includes, for example, a heating lamp, one or more resistive wires or filaments (or twisted wires), metal filaments, metallic strips or rods, and/or other appropriate thermal radical generators or elements that can be heated to a specified temperature (i.e., a molecular cracking temperature) sufficient to thermally crack molecules of the feedstock process gas. The heating element is generally disposed, located or arranged to extend centrally within the body of the thermal cracking apparatus along the central longitudinal axis thereof. For example, if there is only one heating element, then it is placed at or concentric with the central longitudinal axis, and if there is a plurality of the heating elements, then they are spaced or offset generally symmetrically or concentrically at locations near and around and parallel to the central longitudinal axis.

Thermal cracking to produce the carbon nanoparticles and aggregates described herein is generally achieved by passing the feedstock process gas over, in contact with, or within the vicinity of, the heating element within a longitudinal elongated reaction zone generated by heat from the heating element and defined by and contained inside the body to heat the feedstock process gas to or at a specified molecular cracking temperature, e.g., 600-3000° C. or 1600-2200° C. The reaction zone is considered to be the region surrounding the heating element and close enough to the heating element for the feedstock process gas to receive sufficient heat to thermally crack the molecules thereof. The reaction zone is thus generally axially aligned or concentric with the central longitudinal axis of the body. In some embodiments, the thermal cracking is performed under a specified pressure. In some embodiments, the feedstock process gas is circulated around or across the outside surface of a container of the reaction zone or a heating chamber in order to cool the container or chamber and preheat the feedstock process gas before flowing the feedstock process gas into the reaction zone.

In some embodiments, the carbon nanoparticles and aggregates described herein and/or hydrogen gas are produced without the use of catalysts. In other words, the process is catalyst-free.

Some embodiments to produce the carbon nanoparticles and aggregates described herein using thermal cracking apparatuses and methods provide a standalone system that can advantageously be rapidly scaled up or scaled down for different production levels as desired. For example, some embodiments are scalable to provide a standalone hydrogen and/or carbon nanoparticle producing station system, a hydrocarbon source or a fuel cell station. Some embodiments can be scaled up to provide higher capacity systems, e.g., for a refinery or the like.

In some embodiments, a thermal cracking apparatus for cracking a feedstock process gas to produce the carbon nanoparticles and aggregates described herein includes a body, a feedstock process gas inlet, and an elongated heating element. The body has an inner volume with a longitudinal axis. The inner volume has a reaction zone concentric with the longitudinal axis. A feedstock process gas is flowed into the inner volume through the feedstock process gas inlet during thermal cracking operations. The elongated heating element is disposed within the inner volume along the longitudinal axis and is surrounded by the reaction zone. During the thermal cracking operations, the elongated heating element is heated by electrical power to a molecular cracking temperature to generate the reaction zone, the feedstock process gas is heated by heat from the elongated heating element, and the heat thermally cracks molecules of the feedstock process gas that are within the reaction zone into constituent components of the molecules.

In some embodiments, a method for cracking a feedstock process gas to produce the carbon nanoparticles and aggregates described herein includes providing a thermal cracking apparatus having an inner volume that has a longitudinal axis and an elongated heating element disposed within the inner volume along the longitudinal axis; heating the elongated heating element by electrical power to a molecular cracking temperature to generate a longitudinal elongated reaction zone within the inner volume; flowing a feedstock process gas into the inner volume and through the longitudinal elongated reaction zone, wherein the feedstock process gas is heated by heat from the elongated heating element; thermally cracking molecules of the feedstock process gas within the longitudinal elongated reaction zone into constituent components thereof (e.g., hydrogen gas and one or more solid products) as the feedstock process gas flows through the longitudinal elongated reaction zone; and collecting the constituent components.

In some embodiments, the feedstock process gas to produce the carbon nanoparticles and aggregates described herein includes a hydrocarbon gas, and the constituent components include hydrogen and the carbon nanoparticles and aggregates described herein. In some embodiments, the carbon nanoparticles and aggregates include two or more MWSFs and layers of graphene coating the MWSFs, and/or connected MWSFs and layers of graphene coating the connected MWSFs. In some embodiments, the feedstock process gas is preheated (e.g., to 100-500° C.) by flowing the feedstock process gas through a gas preheating region between a heating chamber and a shell of the thermal cracking apparatus before flowing the feedstock process gas into the inner volume. In some embodiments, a gas having nanoparticles therein is flowed into the inner volume and through the longitudinal elongated reaction zone to mix with the feedstock process gas; and a coating of a solid product (e.g., layers of graphene) is formed around the nanoparticles.

Additional information and embodiments for thermal cracking system methods and apparatuses to produce the carbon nanoparticles and aggregates described herein are described in the aforementioned U.S. patent application Ser. No. 15/470,450.

Post-Processing High Purity Carbon Allotropes

In some embodiments, the carbon nanoparticles and aggregates containing multi-walled spherical fullerenes (MWSFs) or connected MWSFs described herein are produced and collected, and no post-processing is done. In other embodiments, the carbon nanoparticles and aggregates containing multi-walled spherical fullerenes (MWSFs) or connected MWSFs described herein are produced and collected, and some post-processing is done. Some examples of post-processing include mechanical processing, such as ball milling, grinding, attrition milling, micro-fluidizing, and other techniques to reduce the particle size without damaging the MWSFs. Some examples of post-processing include exfoliation processes such as sheer mixing, chemical etching, oxidizing (e.g., Hummer method), thermal annealing, doping by adding elements during annealing (e.g., S, and N), steaming, filtering, and lypolizing, among others. Some examples of post-processing include sintering processes such as SPS (Spark Plasma Sintering, i.e., Direct Current Sintering), Microwave, and UV (Ultra-Violet), which can be conducted at high pressure and temperature in an inert gas. In some embodiments, multiple post-processing methods can be used together or in series. In some embodiments, the post-processing will produce functionalized carbon nanoparticles or aggregates containing multi-walled spherical fullerenes (MWSFs) or connected MWSFs.

In some embodiments, the materials are mixed together in different combinations. In some embodiments, different carbon nanoparticles and aggregates containing MWSFs or connected MWSFs described herein are mixed together before post-processing. For example, different carbon nanoparticles and aggregates containing MWSFs or connected MWSFs with different properties (e.g., different sizes, different compositions, different purities, from different processing runs, etc.) can be mixed together. In some embodiments, the carbon nanoparticles and aggregates containing MWSFs or connected MWSFs described herein could be mixed with graphene to change the ratio of the connected MWSFs to graphene in the mixture. In some embodiments, different carbon nanoparticles and aggregates containing MWSFs or connected MWSFs described herein are mixed together after post-processing. For example, different carbon nanoparticles and aggregates containing MWSFs or connected MWSFs with different properties and/or different post-processing methods (e.g., different sizes, different compositions, different functionality, different surface properties, different surface areas) can be mixed together.

In some embodiments, the carbon nanoparticles and aggregates described herein are produced and collected, and subsequently processed by mechanical grinding, milling, or exfoliating. In some embodiments, the processing (e.g., by mechanical grinding, milling, exfoliating, etc.) reduces the average size of the particles. In some embodiments, the processing (e.g., by mechanical grinding, milling, exfoliating, etc.) increases the average surface area of the particles. In some embodiments, the processing by mechanical grinding, milling or exfoliation shears off some fraction of the carbon layers, producing sheets of graphite mixed with the carbon nanoparticles. In some embodiments, the mechanical grinding or milling is performed using a ball mill, a planetary mill, a rod mill, a shear mixer, high-shear granulator, an autogenous mill, or other type of machine used to break solid materials into smaller pieces by grinding, crushing or cutting. In some embodiments, the mechanical grinding, milling or exfoliating is performed wet or dry. In some embodiments, the mechanical grinding is performed by grinding for some period of time, then idling for some period of time, and repeating the grinding and idling for a number of cycles. In some embodiments, the grinding period is from 1 minute to 20 minutes, or from 1 minute to 10 minutes, or from 3 minutes to 8 minutes, or approximately 3 minutes, or approximately 8 minutes. In some embodiments, the idling period is from 1 minute to 10 minutes, or approximately 5 minutes, or approximately 6 minutes. In some embodiments, the number of grinding and idling cycles is from 1 to 100, or from 5 to 100, or from 10 to 100, or from 5 to 10, or from 5 to 20. In some embodiments, the total amount of time grinding and idling is from 10 minutes to 1200 minutes, or from 10 minutes to 600 minutes, or from 10 minutes to 240 minutes, or from 10 minutes to 120 minutes, or from 100 minutes to 90 minutes, or from 10 minutes to 60 minutes, or approximately 90 minutes, or approximately 120 minutes.

In some embodiments, the grinding steps in the cycle are performed by rotating a mill in one direction for a first cycle (e.g., clockwise), and then rotating a mill in the opposite direction (e.g., counter-clockwise) for the next cycle. In some embodiments, the mechanical grinding or milling is performed using a ball mill, and the grinding steps are performed using a rotation speed from 100 to 1000 rpm, or from 100 to 500 rpm, or approximately 400 rpm. In some embodiments, the mechanical grinding or milling is performed using a ball mill using a milling media with a diameter from 0.1 mm to 20 mm, or from 0.1 mm to 10 mm, or from 1 mm to 10 mm, or approximately 0.1 mm, or approximately 1 mm, or approximately 10 mm. In some embodiments, the mechanical grinding or milling is performed using a ball mill using a milling media composed of metal such as steel, an oxide such as zirconium oxide (zirconia), yttria stabilized zirconium oxide, silica, alumina, magnesium oxide, or other hard materials such as silicon carbide or tungsten carbide.

In some embodiments, the carbon nanoparticles and aggregates described herein are produced and collected, and subsequently processed using elevated temperatures, such as thermal annealing, or sintering. In some embodiments, the processing using elevated temperatures is done in an inert environment such as nitrogen or argon. In some embodiments, the processing using elevated temperatures is done at atmospheric pressure, or under vacuum, or at low pressure. In some embodiments, the processing using elevated temperatures is done at a temperature from 500° C. to 2500° C., or from 500° C. to 1500° C., or from 800° C. to 1500° C., or from 800° C. to 1200° C., or from 800° C. to 1000° C., or from 2000 to 2400° C., or approximately 800° C., or approximately 1000° C., or approximately 1500° C., or approximately 2000° C., or approximately 2400° C.

In some embodiments, the carbon nanoparticles and aggregates described herein are produced and collected, and subsequently additional elements or compounds are added, thereby incorporating the unique properties of the carbon nanoparticles and aggregates into other mixtures of materials. For example, nickel can be added to increase the magnetic permeability of the carbon nanoparticles and aggregates, or the degree of magnetization that the carbon nanoparticles and aggregates obtain in response to an applied magnetic field. Another example is the addition of sulfur to increase the surface area of the carbon nanoparticles and aggregates by forcing the carbon layers to separate. For example, adding sulfur can increase the surface area by 2 or 3 times compared with the material without sulfur. Another method to increase the surface area is through oxidation, however, the resulting compounds (e.g., graphene oxide) are insulators. The methods described herein, e.g., using sulfur, can produce particles with high surface areas that are conductive.

In some embodiments, either before or after post-processing, the carbon nanoparticles and aggregates described herein are added to solids, liquids or slurries of other elements or compounds to form additional mixtures of materials incorporating the unique properties of the carbon nanoparticles and aggregates. In some embodiments, the carbon nanoparticles and aggregates described herein are mixed with other solid particles, polymers or other materials. The resulting powders or composites of the particles in a solid matrix of a different material, can be used in different applications, such as in lubricants or structural composite materials. In some embodiments, the carbon nanoparticles and aggregates described herein are mixed with liquids to produce inks for different applications, such as conductive inks. The resulting inks can also be coated on a substrate or infused in another material for various applications such as capacitor or battery electrodes. In some embodiments, the carbon nanoparticles and aggregates described herein are mixed with solvents and optionally other particles to create slurries, which can then be coated or printed onto other surfaces in various applications, such as printed conductor antennas.

In some embodiments, either before or after post-processing, the carbon nanoparticles and aggregates described herein are used in various applications, including but not limited to lubricant formulations (e.g., lubricants for high-speed or high-stress applications, lubricants for high-temperature environments, lubricants for high-thermal conductivity applications, and anti-stiction lubricants, among others), filtration and separation applications (e.g., chemical filters, water filtration, desalinization, gas separation, oxidation barrier, impermeable membranes, non-reactive filters, and carbon sequestration material, among others), transportation and industrial applications (e.g., rubber additives, tire additives, automobile tire additives, major components in tires, functionalized additives for tires, couplings, mounts, elastomeric o-rings, hoses, sealants, and epoxies, among others), metamaterials formulations (e.g., the particles or aggregates decorated with Ni, Co or Fe nanowires, carbon dielectric layered materials, and interface materials with functionalized surfaces, among other combinations with other materials that result in unexpected properties), electronics ink formulations (e.g., conductive inks, transparent conductive inks, 3D printed circuits and PCBs, resistivity inks, dielectric inks, flexible electronics, piezoelectrics, antennas, rectennas, smart rectennas, electrochromic devices, triboelectric devices, microwave equipment, system inks, and identification systems, among others), other inks (e.g., cosmetics, and 3D printed structural inks, among others), coatings (e.g., anti-corrosion, super hydrophobic, room heating, de-icing, cooling, electro-static discharge (ESD), radiofrequency shielding (EMF shielding) radiofrequency absorbing (EMF absorbing), and fabric and textile coatings, among others), capacitor material formulations (e.g., super capacitor additives, high surface area carbon, high purity carbon, high surface area high purity carbon, and separators, among others), sensors and solid state electronics applications (e.g., chemical, humidity, touch, light, transistors, diodes, and integrated devices, among others), composite materials formulations (e.g., as additives for cement, steel, aluminum, plastics, and carbon fiber, among others), energy applications (e.g., hydrogen storage, anode composites, cathode composites, batteries, fuel cell electrodes, capacitors, and capacitor/battery hybrids, among others), in-vivo bio-medical applications (e.g., tissue engineering, drug delivery, metal delivery, bio-degradable nanowire for neuro regeneration, and better health, among others), and ex-vivo bio-medical applications (e.g., filtration, skin electrodes, and other medical devices).

EXAMPLES

Example 1: Experimental Data from Thermal Hot-Wire Processing System

For this example, the carbon nanoparticles were generated using a thermal cracking apparatus, described in embodiments above. The thermal cracking apparatus had a main body made from stainless steel with a quartz inner wall material, and a heating element that includes a tantalum/tungsten resistive wire. The reaction zone volume was approximately 2000 $cm^3$. The precursor material was methane, and was flowed from 5 to 10 slm. With those flow rates and the tool geometry, the resonance time of the gas in the reaction chamber was from approximately 0.1 second to 10 seconds, and the carbon particle production rate was from approximately 140 g/hr.

Figure 3A:
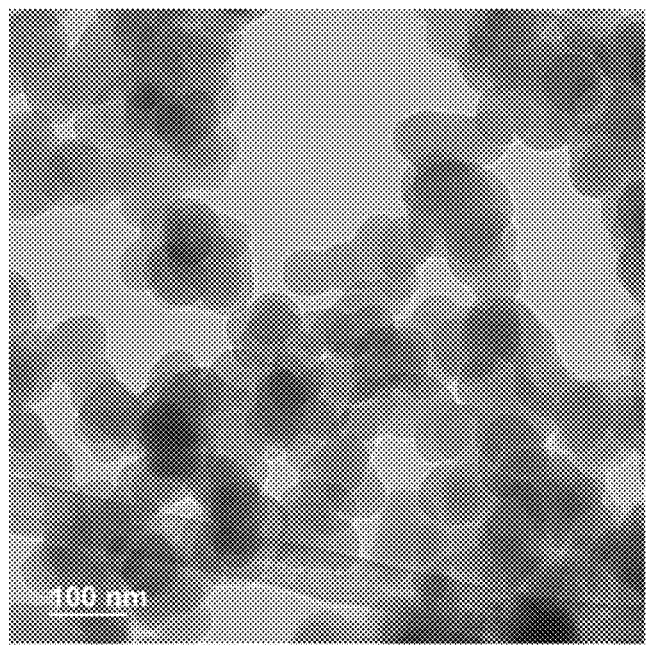
FIGS. 3A-3C show TEM images and Raman spectra from as-synthesized carbon aggregates in a first example, in accordance with some embodiments.
Figure 3B:
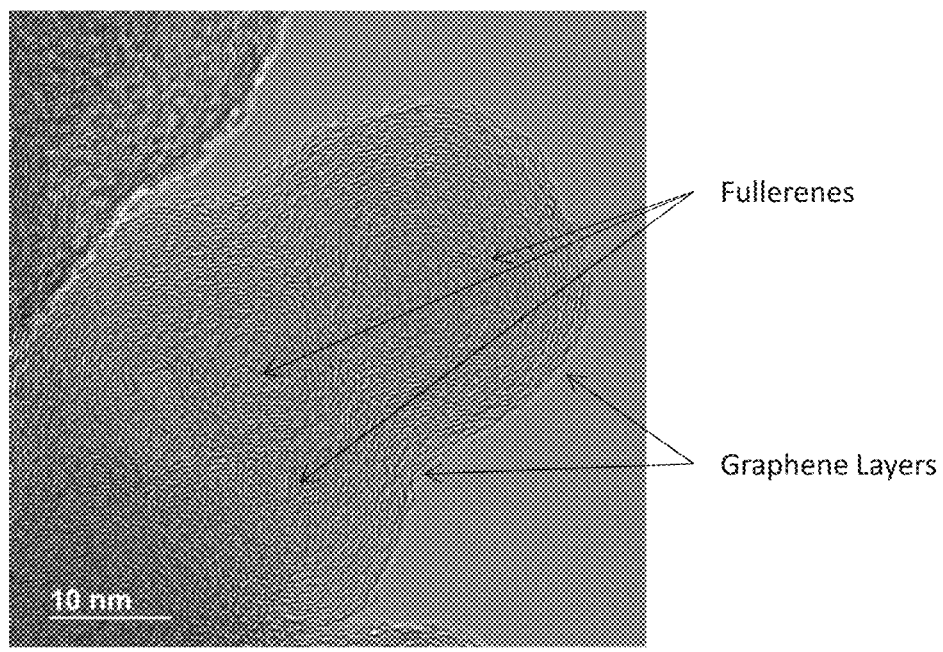

FIGS. 3A and 3B show TEM images of as-synthesized carbon nanoparticles of this example. The carbon nanoparticles contain connected multi-walled spherical fullerenes (MWSFs) with layers of graphene coating the connected MWSFs.

Figure 3C:
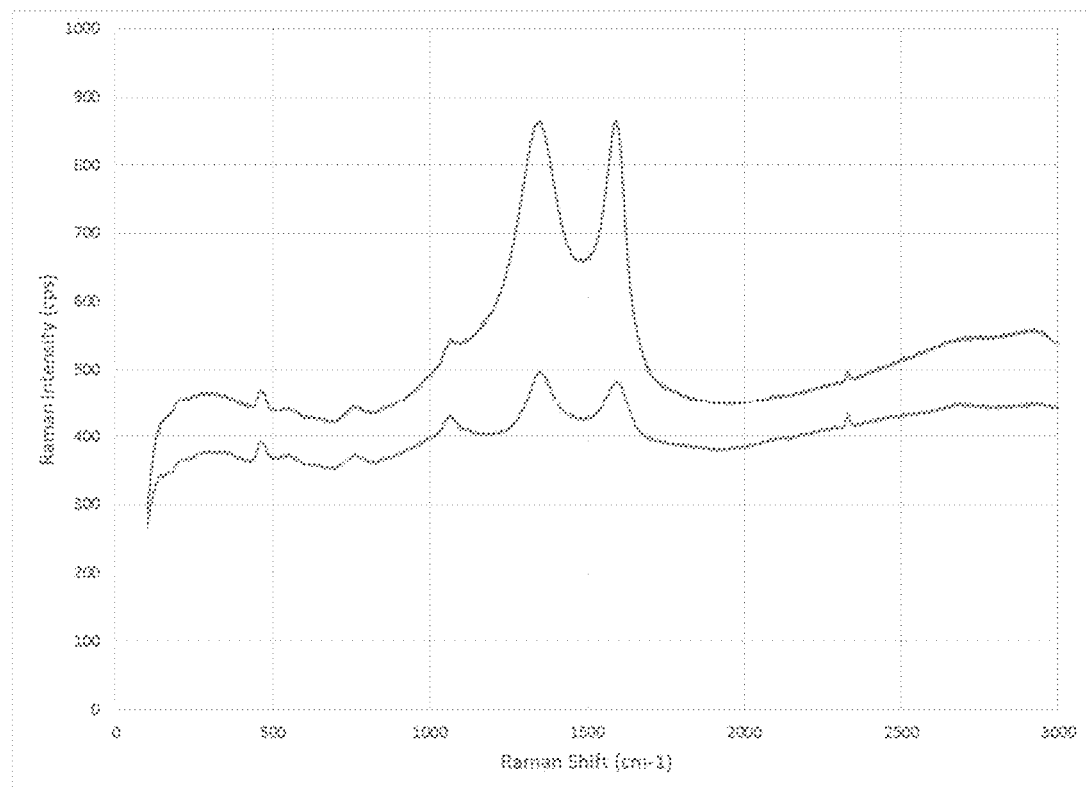

The ratio of MWSF to graphene allotropes in this example is approximately 80%, due to the relatively short resonance times. The MWSFs in FIG. 3A are approximately 5-10 nm in diameter, and the diameter can be from 5 to 500 nm using the conditions described above. In some embodiments, the average diameter across the MWSFs is in a range from 5 to 500 nm, or from 5 to 250 nm, or from 5 to 100 nm, or from 5 to 50 nm, or from 10 to 500 nm, or from 10 to 250 nm, or from 10 to 100 nm, or from 10 to 50 nm, or from 40 to 500 nm, or from 40 to 250 nm, or from 40 to 100 nm, or from 50 to 500 nm, or from 50 to 250 nm, or from 50 to 100 nm. No catalyst was used in this process, and therefore, there is no central seed containing contaminants. The aggregate particles produced in this example had particle size of approximately 10 to 100 microns, or approximately 10 to 500 microns. FIG. 3C shows the Raman spectrum of the as-synthesized aggregates in this example taken with 532 nm incident light. The ID/IG for the aggregates produced in this example is from approximately 0.99 to 1.03, indicating that the aggregates were composed of carbon allotropes with a high degree of order.

Figure 4A:
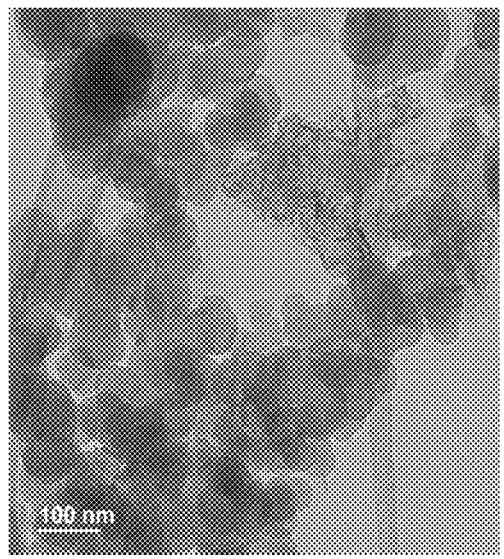
FIGS. 4A-4C show TEM images and Raman spectra from size-reduced carbon aggregates in a first example, in accordance with some embodiments.
Figure 4B:
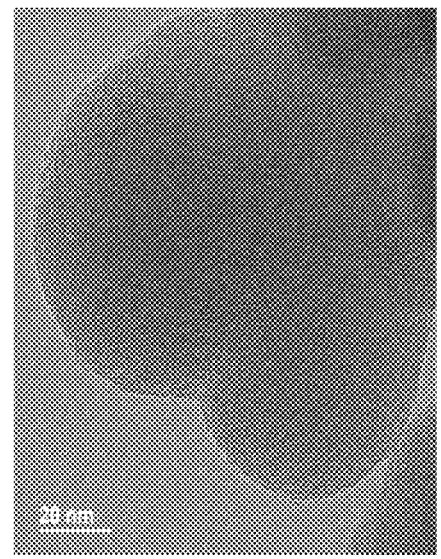
Figure 4C:
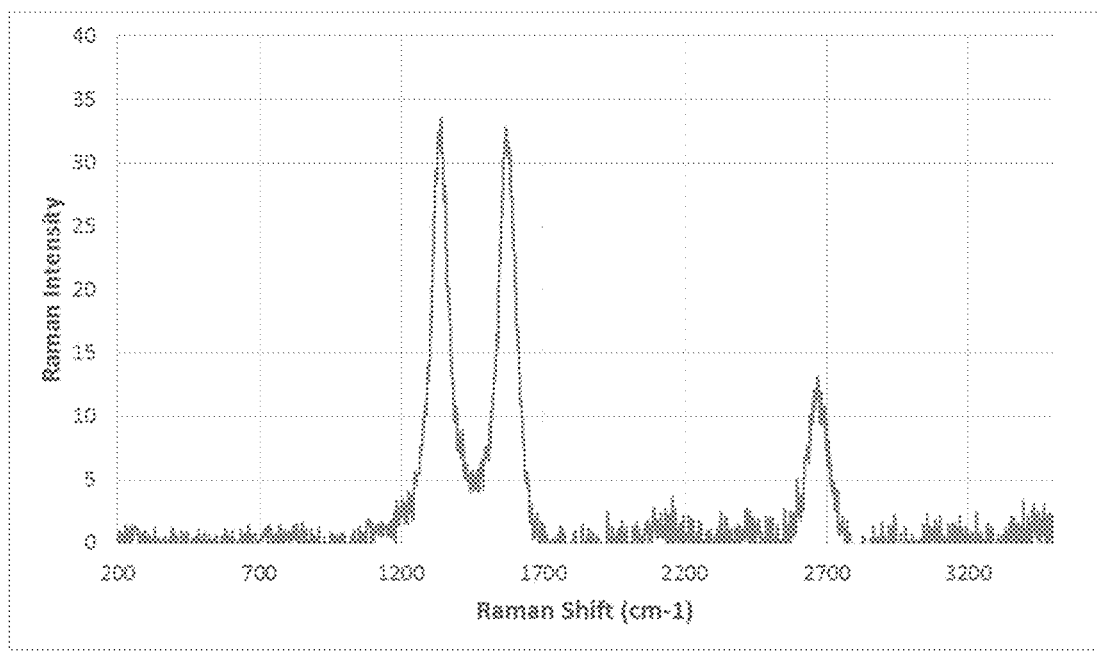

FIGS. 4A and 4B show TEM images of the carbon nanoparticles of this example after size-reduction by grinding in a ball mill. The ball milling was performed in cycles with a 3 minute counter-clockwise grinding step, followed by a 6 minute idle step, followed by a 3 minute clockwise grinding step, followed by a 6 minute idle step. The grinding steps were performed using a rotation speed of 400 rpm. The milling media was zirconia, and ranged in size from 0.1 mm to 10 mm. The total size reduction processing time was from 60 to 120 minutes. After size-reduction, the aggregate particles produced in this example had particle size of approximately 1 to 5 microns. The carbon nanoparticles after size-reduction are connected MWSFs with layers of graphene coating the connected MWSFs. FIG. 4C shows a Raman spectrum from the aggregates of this example after size-reduction taken with a 532 nm incident light. The ID/IG for the aggregate particles in this example after size-reduction is approximately 1.04. Additionally, the particles after size-reduction had a Brunauer, Emmett and Teller (BET) specific surface area of approximately 40 to 50 $m^2/g$.

The purity of the aggregates produced in this sample were measured using mass spectrometry and x-ray fluorescence spectroscopy (XRF). The ratio of carbon to other elements, except for H, measured in 16 different batches was from 99.86% to 99.98%, with an average of 99.94%.

Example 2: Experimental Data from Thermal Hot-Wire Processing System

In this example, carbon nanoparticles were generated using a thermal hot-wire processing system described in Example 1. The precursor material was methane, and was flowed from 1 to 5 slm. With those flow rates and the tool geometry, the resonance time of the gas in the reaction chamber was from approximately 20 second to 30 seconds, and the carbon particle production rate was from approximately 20 g/hr.

Figure 5A:
FIGS. 5A-5D show TEM images and Raman spectra from as-synthesized carbon aggregates in a second example, in accordance with some embodiments.
Figure 5B:
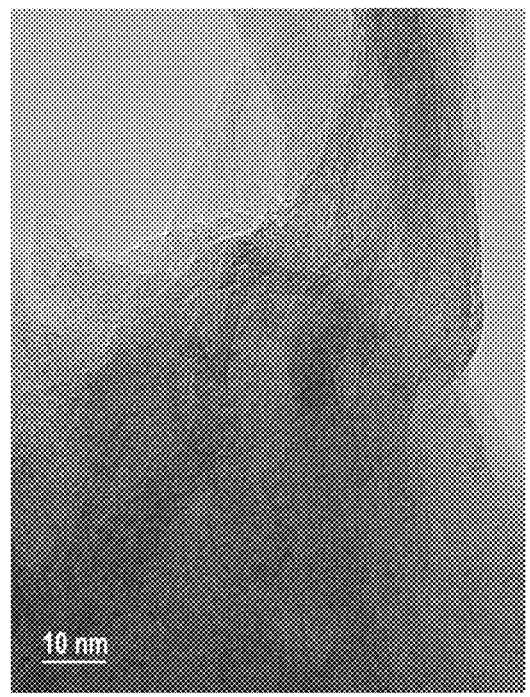
Figure 5C:
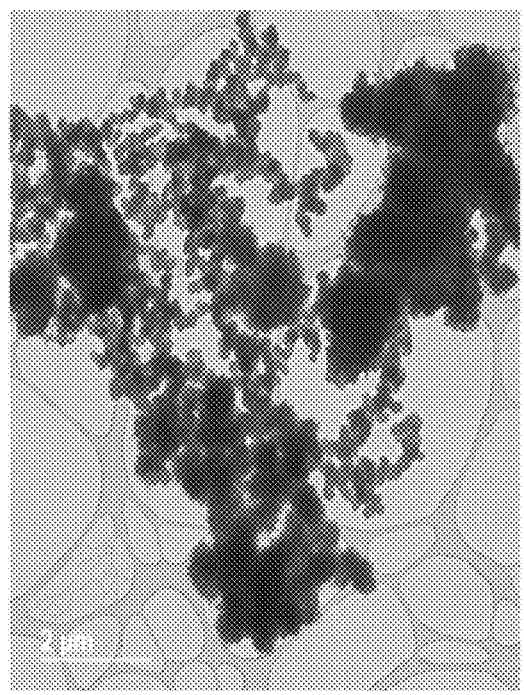
Figure 5D:
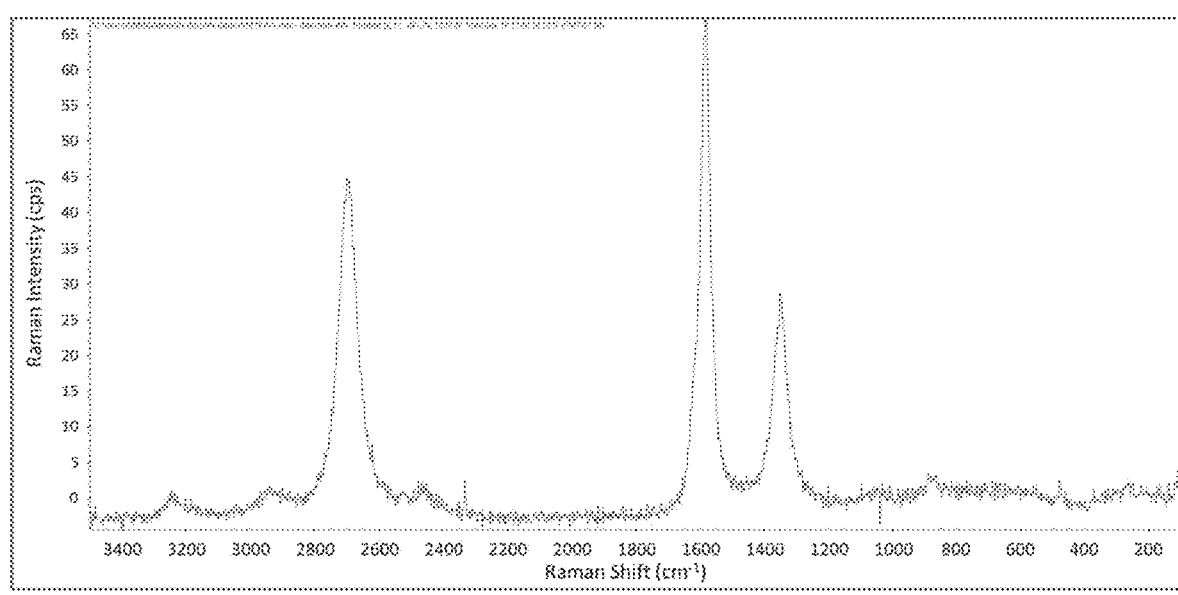

FIGS. 5A, 5B and 5C show TEM images of as-synthesized carbon nanoparticles of this example. The carbon nanoparticles contain connected multi-walled spherical fullerenes (MWSFs) with layers of graphene coating the connected MWSFs. The ratio of multi-walled fullerene to graphene allotropes in this example is approximately 30%, due to the relatively long resonance times allowing thicker, or more, layers of graphene to coat the MWSFs. No catalyst was used in this process, and therefore, there is no central seed containing contaminants. The as-synthesized aggregate particles produced in this example had particle size of approximately 10 to 500 microns. FIG. 5D shows a Raman spectrum from the aggregates of this example. The Raman signature of the as-synthesized particles in this example is indicative of the thicker graphene layers which coat the MWSFs in the as-synthesized material. Additionally, the as-synthesized particles had a Brunauer, Emmett and Teller (BET) specific surface area of approximately 90 to 100 $m^2/g$.

Figure 6A:
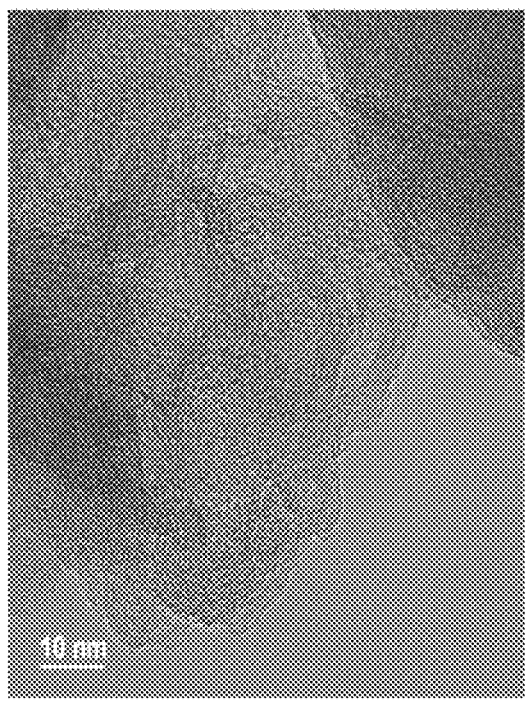
FIGS. 6A-6C show TEM images and Raman spectra from size-reduced carbon aggregates in a second example, in accordance with some embodiments.
Figure 6B:
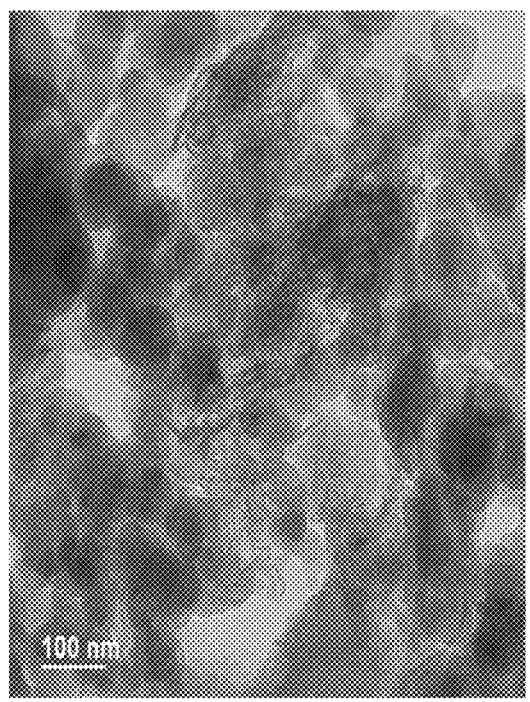
Figure 6C:
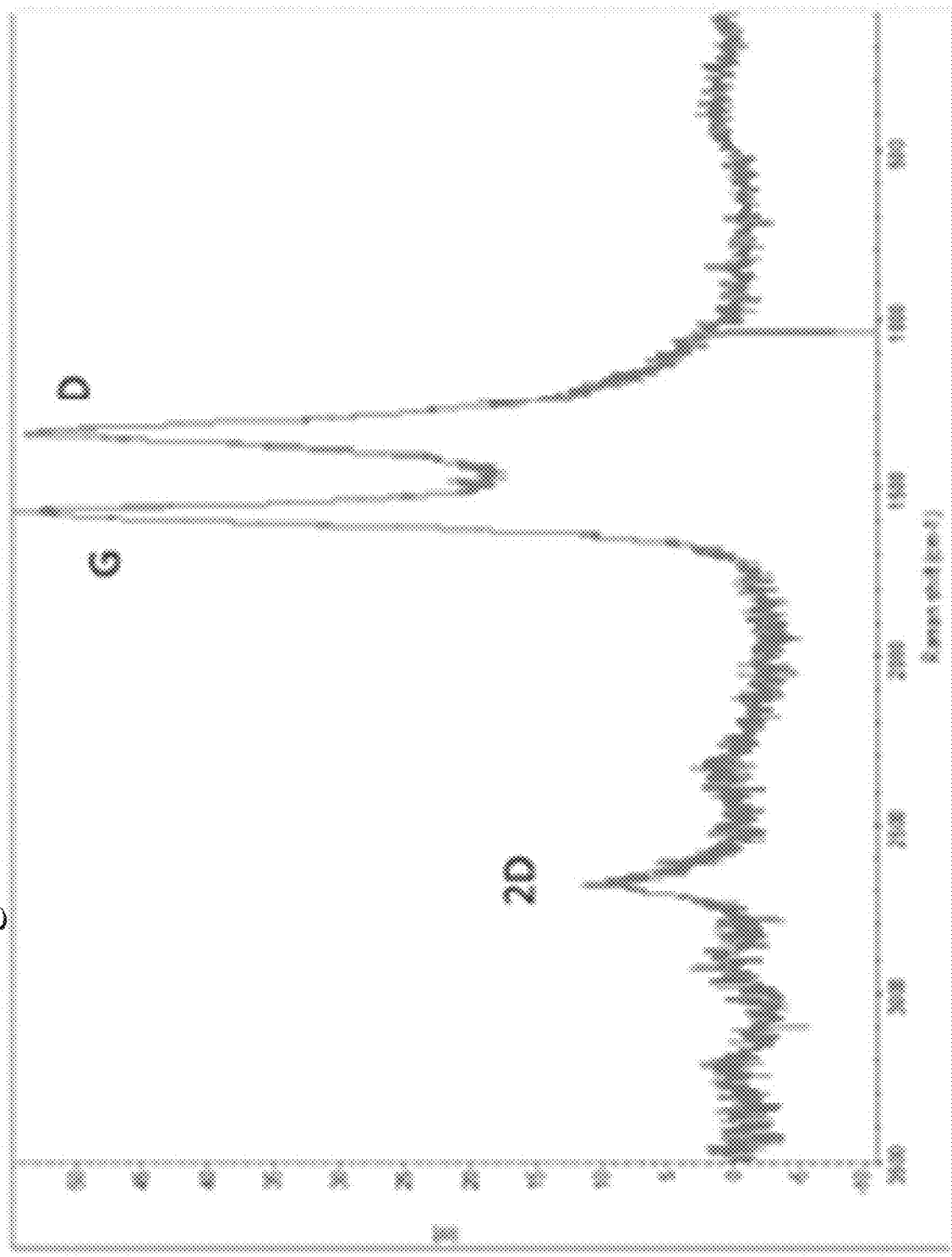

FIGS. 6A and 6B show TEM images of the carbon nanoparticles of this example after size-reduction by grinding in a ball mill. The size-reduction process conditions were the same as those described in Example 1. After size-reduction, the aggregate particles produced in this example had particle size of approximately 1 to 5 microns. The TEM images show that the connected MWSFs that were buried in the graphene coating can be observed after size-reduction. FIG. 6C shows a Raman spectrum from the aggregates of this example after size-reduction taken with 532 nm incident light. The ID/IG for the aggregate particles in this example after size-reduction is approximately 1, indicating that the connected MWSFs that were buried in the graphene coating as-synthesized had become detectable in Raman after size-reduction and were well-ordered. The particles after size-reduction had a Brunauer, Emmett and Teller (BET) specific surface area of approximately 90 to 100 m²/g.

Example Thermal Cracking Apparatuses

FIG. 7 depicts a simplified schematic view of a thermal cracking apparatus 1500, in accordance with at least some embodiments. The thermal cracking apparatus 1500 generally includes a body 1502, a top cap assembly 1504, a bottom cap assembly 1506, a heating element 1508, a feedstock process gas preheat inlet 1512, a secondary feedstock process gas inlet 1514, one or more cooling gas inlets and outlets 1516 and 1518, a cooling fluid inlet and outlet 1520 and 1522, and a product outlet 1524, among other components shown (but not labeled) or not shown for simplicity and ease of illustration and description.

The body 1502 generally includes an outer shell or housing 1526, a secondary shell 1528, an inner reactor tube (an insert or heating chamber) 1530, and an outer reactor tube 1532. The body 1502 is considered a dual wall structure or dual tube reactor because it generally includes both of the reactor tubes 1530 and 1532 disposed within the shells 1526 and 1528. (In some embodiments, the outer reactor tube 1532 is considered to be another shell surrounding the inner reactor tube 1530.) The shells 1526 and 1528 and the reactor tubes 1530 and 1532 are generally cylindrical in shape with a central longitudinal axis arranged vertically. The inner reactor tube 1530 is generally made of quartz, alumina, or other appropriate material for withstanding the operational temperatures of the reaction zone. The shells 1526 and 1528 and the outer reactor tube 1532 are generally made of steel, titanium, or other appropriate materials.

The top cap assembly 1504 and the bottom cap assembly 1506 are generally made of steel or other appropriate materials. The top cap assembly 1504 and the bottom cap assembly 1506 are mounted or attached to the top and bottom, respectively, of the shells 1526 and 1528 to hold the shells 1526 and 1528 in a generally concentric arrangement or relationship to each other with a space 1534 there between. The space 1534 between the shells 1526 and 1528 defines a cooling fluid region.

A top and bottom plug, cap or insert 1536 and 1538 are disposed within the secondary shell 1528 near the top and bottom, respectively, of the body 1502. The top and bottom plugs 1536 and 1538 are generally made of steel or other appropriate materials. The bottom plug 1538 is mounted or set within the secondary shell 1528 down against an inner surface or flange of the bottom cap assembly 1506 and engages bottom ends of the reactor tubes 1530 and 1532. The top plug 1536 is mounted or set within the secondary shell 1528 near a top end of the secondary shell 1528 and engages top ends of the reactor tubes 1530 and 1532. A compression spring assembly 1540 engages the top plug 1536 and an inner surface or flange of the top cap assembly 1504 to press the top plug 1536 to the reactor tubes 1530 and 1532, the reactor tubes 1530 and 1532 to the bottom plug 1538, and the bottom plug 1538 to the inner surface or flange of the bottom cap assembly 1506, thereby holding the reactor tubes 1530 and 1532 in place. The top and bottom plugs 1536 and 1538 generally hold the reactor tubes 1530 and 1532 in a generally concentric arrangement or relationship to each other and to the secondary shell 1528, with a space 1542 between the outer reactor tube 1532 and the secondary shell 1528, and a space 1544 between the inner reactor tube 1530 and the outer reactor tube 1532. The space 1542 between the outer reactor tube 1532 and the secondary shell 1528 defines a gas coolant region. The space 1544 between the inner reactor tube 1530 and the outer reactor tube 1532 defines a feedstock gas preheating region.

The heating element 1508 is any appropriate type described above and extends along, generally concentrically with, and parallel to, the central longitudinal axis of the body 1502 or the inner reactor tube 1530. The heating element 1508 is mounted or attached at a top end to a top electrode assembly 1546 that is mounted or attached to the body 1502 and extends through the shells 1526 and 1528 above the top plug 1536. In the illustrated embodiment, the heating element 1508 is mounted or attached at a bottom end to a bottom electrode assembly 1548 and a spring bias assembly 1550. The bottom electrode assembly 1548 is mounted or attached to a lower portion 1552 of the bottom cap assembly 1506 and extends through the lower portion 1552 to contact the heating element 1508 through a hole in the bottom electrode assembly 1548. The spring bias assembly 1550 includes a spring 1554 within a cylindrical housing 1556 that is attached or mounted to the underside of the lower portion 1552 of the bottom cap assembly 1506. The heating element 1508 extends through a hole in the bottom cap assembly 1506 and the hole in the bottom electrode assembly 1548 down to the bottom of the spring 1554. The heating element 1508 is attached to the bottom of the spring 1554 and is held in tension by the spring 1554 acting against the underside of the bottom electrode assembly 1548. Thus, when the heating element 1508 heats up during gas processing or thermal cracking operations and cools down afterwards, any thermal expansion or contraction of the heating element 1508 is compensated for by the spring bias assembly 1550, which maintains the heating element 1508 in tension, so that the heating element 1508 remains generally concentric and parallel to the central longitudinal axis of the body 1502 or the inner reactor tube 1530.

An interior surface of a wall of the inner reactor tube 1530 defines an inner volume, all or part of which includes a longitudinal elongated reaction zone generated in the vicinity of the heating element 1508 during gas processing or thermal cracking operations. The inner reactor tube 1530 is thus the heating or reaction chamber of the thermal cracking apparatus 1500, and the central longitudinal axis of the body 1502 or the inner reactor tube 1530 is also considered to be a central longitudinal axis of the longitudinal elongated reaction zone.

Electrical power is provided to the heating element 1508 through the top electrode assembly 1546 and the bottom electrode assembly 1548 during gas processing operations. The top electrode assembly 1546 electrically connects to, or near, the top of the heating element 1508. The bottom electrode assembly 1548 electrically connects to, or near, the bottom of the heating element 1508, either directly to the heating element 1508 (within the hole therein) or through an electrical connection to the spring 1554.

The feedstock process gas preheat inlet 1512 is fluidly connected to a feedstock process gas source (not shown). The feedstock process gas preheat inlet 1512 is also attached or mounted to the shells 1526 and 1528 to be in fluid communication with the feedstock gas preheating region (space 1544) via apertures or holes through the shells 1526 and 1528, the bottom plug 1538, and the outer reactor tube 1532. During gas processing operations, the feedstock process gas is flowed from the source through the feedstock process gas preheat inlet 1512 and into the feedstock process gas preheating region (space 1544). The feedstock process gas then circulates across the outer surface of the inner reactor tube 1530. The inner reactor tube 1530 is typically very hot due to the thermal gas processing occurring therein. The circulation of the feedstock process gas around the inner reactor tube 1530, thus, serves the dual purpose of cooling the inner reactor tube 1530 and preheating the feedstock process gas with residual heat transferred through the wall of the inner reactor tube 1530 from the reaction zone. For embodiments in which the gas flow direction is downward, a series of holes or apertures 1558 in the wall of the inner reactor tube 1530 near the top of the feedstock gas preheating region (space 1544) allow the preheated feedstock process gas to flow into the inner volume of the inner reactor tube 1530, i.e., the reaction zone. Within the inner volume or the reaction zone, the preheated feedstock process gas circulates around the heating element 1508, which further heats the feedstock process gas in the vicinity thereof to thermally crack the feedstock process gas into constituent elements and/or lower order molecules, i.e., the gaseous and solid products. For embodiments in which the gas flow direction is upward, on the other hand, the series of holes or apertures 1558 in the wall of the inner reactor tube 1530 are placed near the bottom of the feedstock gas preheating region (space 1544) and the feedstock process gas preheat inlet 1512 is placed near the top of the feedstock gas preheating region.

In some embodiments, the secondary feedstock process gas inlet 1514 is fluidly connected to a source (not shown) of a gas (e.g., a second feedstock process gas) having additional particles (e.g., nanoparticles of Silicon (Si), Silicon Carbide (SiC), or other appropriate materials able to withstand the high temperatures of the process without melting) floating or suspended therein. The secondary feedstock process gas inlet 1514 is attached or mounted to the shells 1526 and 1528 to be in fluid communication with the inner volume of the inner reactor tube 1530 via apertures through the shells 1526 and 1528, the top plug 1536, and the inner reactor tube 1530. During gas processing operations, the feedstock process gas with additional particles is flowed from the source through the secondary feedstock process gas inlet 1514, through a series of holes or apertures 1560 (in the wall of the inner reactor tube 1530 near the top thereof), and into the inner volume of the inner reactor tube 1530, i.e., the reaction zone. Within the inner volume or the reaction zone, the feedstock process gas with additional particles mixes with the preheated feedstock process gas. In some embodiments, the additional particles have a melting point at or above about 500-1000° C. The temperature to which the additional particles are heated generally depends on various process parameters, such as the temperature of the heating element 1508, the flow rate of the feedstock process gas, the longitudinal length of the reaction zone, and the time that the additional particles spend within the reaction zone. Therefore, since the process parameters are set so that the additional particles are heated to a temperature lower than their melting point when they pass through the reaction zone, the solid carbon product (e.g., the graphene) produced from the feedstock process gas (e.g., the methane, natural gas, or other hydrocarbons) generally forms a coating around the additional particles. The coating generally includes one or more layers of the solid carbon product, such as one or more concentric layers of graphene, surrounding each additional particle. In this manner, carbon-coated nanoparticles are formed within the reaction zone. Additionally, in some embodiments, the additional particles act as a catalyst in the thermal cracking of the feedstock process gas in the reaction zone.

In some embodiments, the feedstock process gas having additional particles, the secondary feedstock process gas inlet 1514, and the series of holes or apertures 1560 are considered optional or are not included in the thermal cracking apparatus 1500.

In some embodiments, the cooling gas inlet and outlet 1516 and 1518 are attached or mounted to the shells 1526 and 1528 to be in fluid communication with the gas coolant region, i.e., the space 1542 between the outer reactor tube 1532 and the secondary shell 1528, via apertures or holes through the shells 1526 and 1528. During gas processing operations, a coolant gas (e.g., air, nitrogen, a noble gas, etc.) is flowed from a source thereof, through the cooling gas inlet 1516, and into the gas coolant region (space 1542). The coolant gas thus circulates within the gas coolant region, absorbs some of the heat from the outer reactor tube 1532 (thereby serving to cool the outer reactor tube 1532), and exits through the outlet 1518 to be cooled, recycled, discarded or stored.

In some other embodiments, the space 1542 between the outer reactor tube 1532 and the secondary shell 1528 is filled with a thermally insulating or conducting material, rather than having a coolant gas flow therein. In various embodiments, the use or selection of the coolant gas or the thermally insulating or conducting material for the space 1542 generally depends on the thermal requirements for the overall configuration of the thermal cracking apparatus 1500, the type of the feedstock process gas, the type or characteristics of the desired solid and/or gaseous products, and/or the process parameters of the gas processing operations. Different embodiments, in other words, generally have different thermal requirements.

In some embodiments, the cooling fluid inlet and outlet 1520 and 1522 are attached or mounted to the outer shell 1526 to be in fluid communication with the cooling fluid region, i.e., the space 1534 between the shells 1526 and 1528, via apertures or holes through the outer shell 1526. During gas processing operations, a coolant fluid (e.g., water, etc.) is flowed from a source thereof, through the cooling fluid inlet 1520, and into the cooling fluid region (space 1534). The coolant fluid thus circulates within the cooling fluid region, absorbs some of the heat from the secondary shell 1528 (thereby cooling the secondary shell 1528), and exits through the outlet 1522 to be cooled, recycled, discarded or stored. In this manner, the action of the coolant fluid, or the combined action of the coolant fluid and the coolant gas, ensures that the outer surface of the thermal cracking apparatus 1500 (i.e., of the body 1502 or the outer shell 1526) remains cool, or does not become too hot to pose a danger to nearby equipment or personnel.

In the illustrated embodiment, the product outlet 1524 is mounted or attached to the lower portion 1552 of the bottom cap assembly 1506 for embodiments in which the gas flow direction is downward. (For embodiments in which the gas flow direction is upward, on the other hand, the product outlet 1524 is mounted or attached near the top of the inner volume of the inner reactor tube 1530.) The solid and gaseous products generally flow out the bottom cap assembly 1506, e.g., through a series of passageways through the bottom cap assembly 1506 leading to the product outlet 1524, and then to an appropriate storage apparatus, hopper, or other receiving mechanism 1562. In some embodiments, the gaseous and solid products enter the hopper 1562 and are exhausted with a Venturi assist and a flow of nitrogen gas. The solid products are removed by detaching the hopper 1562 from the product outlet 1524 and pouring them out. The gaseous products are removed by flowing through a gaseous product outlet 1564 from the hopper 1562. The gaseous product outlet 1564 is mounted or attached to the hopper 1562 to provide a fluid connection to the interior of the hopper 1562. The gaseous product outlet 1564 is also fluidly connected to a downstream storage apparatus or further gas processing apparatus. The gaseous products are thus flowed out through the gaseous product outlet 1564 to the downstream storage apparatus or further gas processing apparatus. Some embodiments incorporating an alternative exhaust system technique that may be used with the thermal cracking apparatus 1500, with appropriate adjustments or modifications thereto, are described below with respect to FIG. 8. Additionally, in some embodiments, different hoppers (e.g., having the same or different design or configuration) are used for different applications. For example, one hopper is used when producing the solid carbon products, and a different hopper is used when producing the carbon-coated nano-particles. Thus, the bottom cap assembly 1506 and the connection to the product outlet 1524 and/or the hopper 1562 are designed for removal and replacement of the hopper 1562, so that a clean or different hopper 1562 can be attached for each application.

In some situations, some of the solid products can accumulate within the inner volume of the inner reactor tube 1530, e.g., on the interior surface of the wall of the inner reactor tube 1530 and/or the heating element 1508. Some embodiments may also use any appropriate structures or subassemblies for forcibly removing the solid products or cleaning the reaction zone.

Figure 8:
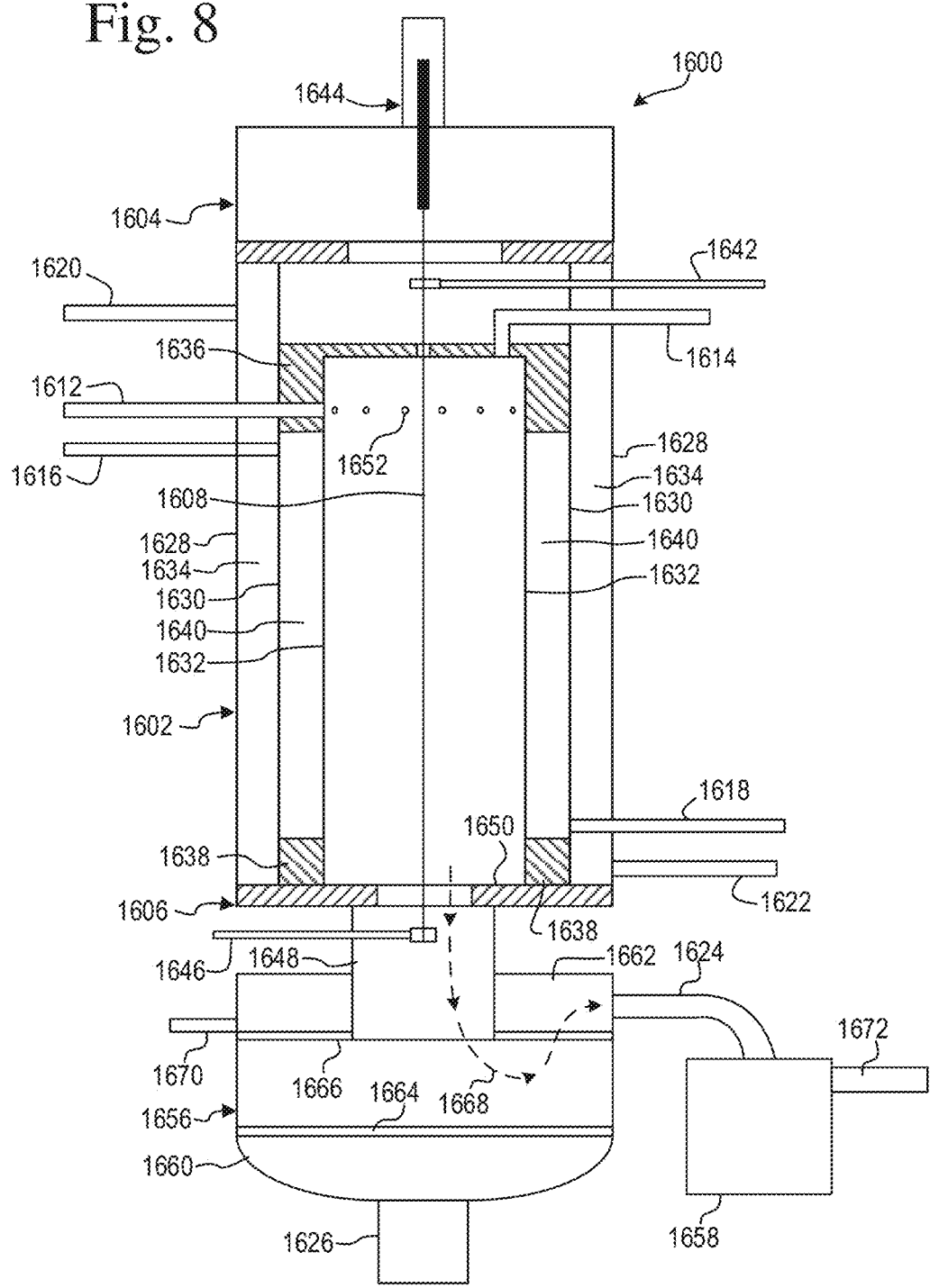
FIG. 8 depicts a simplified schematic view of a cracking apparatus in accordance with at least some embodiments.

FIG. 8 depicts a simplified schematic view of a thermal cracking apparatus 1600, in accordance with at least some embodiments. Some of the features described for the thermal cracking apparatus 1600 can be applied to the embodiment shown for the thermal cracking apparatus 1500 in FIG. 7, and some of the features described above for the thermal cracking apparatus 1500 can be applied to the embodiment for the thermal cracking apparatus 1600, as will be described below.

The thermal cracking apparatus 1600 generally includes a body 1602, a top cap assembly 1604, a bottom cap assembly 1606, a heating element 1608, a feedstock process gas inlet 1612, a secondary feedstock process gas inlet 1614, one or more cooling gas inlets and outlets 1616 and 1618, a cooling fluid inlet and outlet 1620 and 1622, a gaseous product outlet 1624, and a solid product outlet 1626, among other components shown (but not labeled) or not shown for simplicity and ease of illustration and description.

The body 1602 generally includes an outer shell or housing 1628, a secondary shell 1630, and a reactor tube (heating chamber) 1632. The body 1602 is considered a single wall structure or single tube reactor because it generally includes only the the single reactor tube 1632 disposed within the shells 1628 and 1630. The single wall structure or single tube reactor embodiment of FIG. 8 is, thus, an alternative to the dual wall structure or dual tube reactor embodiment of FIG. 7. The shells 1628 and 1630 and the reactor tube 1632 are generally cylindrical in shape with a central longitudinal axis arranged vertically. The reactor tube 1632 is generally made of quartz, alumina, or other appropriate material for withstanding the operational temperatures of the reaction zone. The shells 1628 and 1630 are generally made of steel, titanium, or other appropriate materials.

The top cap assembly 1604 and the bottom cap assembly 1606 are generally made of steel or other appropriate materials. The top cap assembly 1604 and the bottom cap assembly 1606 are mounted or attached to the top and bottom, respectively, of the shells 1628 and 1630 to hold the shells 1628 and 1630 in a generally concentric arrangement or relationship to each other with a space 1634 there between. The space 1634 between the shells 1628 and 1630 defines a cooling fluid region.

A top and bottom plug, cap or insert 1636 and 1638 are disposed within the secondary shell 1630 near the top and bottom, respectively, of the body 1602. The top and bottom plugs 1636 and 1638 are generally made of steel or other appropriate materials. The bottom plug 1638 is mounted or set within the secondary shell 1630 down against an inner surface or flange of the bottom cap assembly 1606 and engages a bottom end of the reactor tube 1632. The top plug 1636 is mounted or set within the secondary shell 1630 near a top end of the secondary shell 1630 and engages a top end of the reactor tube 1632. The reactor tube 1632 and the top and bottom plugs 1636 and 1638 are generally held in place by any appropriate means, e.g., such as that described above for FIG. 7. The top and bottom plugs 1636 and 1638 generally hold the reactor tube 1632 in a generally concentric arrangement or relationship to the secondary shell 1630, with a space 1640 between the reactor tube 1632 and the secondary shell 1630. The space 1640 between the reactor tube 1632 and the secondary shell 1630 defines a gas coolant region.

The heating element 1608 is any appropriate type described above and extends along, generally concentrically with, and parallel to, the central longitudinal axis of the body 1602 or the reactor tube 1632. The heating element 1608 (at or near the top end thereof) contacts a top electrode assembly 1642 that is mounted or attached to the body 1602 and extends through the shells 1628 and 1630 above the top plug 1636. Additionally, the heating element 1608 is mounted or attached at a top end to a tensioning assembly 1644 (e.g., a pneumatic tensioning device, a spring biasing assembly, etc.) through a hole in the top electrode assembly 1642 and a hole in a lower portion of the top cap assembly 1604. The heating element 1608 is also mounted or attached at a bottom end to a bottom electrode assembly 1646. The bottom electrode assembly 1646 is mounted or attached to a lower portion 1648 of the bottom cap assembly 1606 and extends through the lower portion 1648 to connect to the heating element 1608 at a point along a longitudinal axis of the lower portion 1648, which is coaxial with the longitudinal axis of the body 1602 or the reactor tube 1632. The heating element 1608 extends through a hole in a flange 1650 of the bottom cap assembly 1606 down to the bottom electrode assembly 1646. The heating element 1608 is held in tension by the tensioning assembly 1644 acting against an upper portion of the top cap assembly 1604. Thus, when the heating element 1608 heats up during gas processing or thermal cracking operations and cools down afterwards, any thermal expansion or contraction of the heating element 1608 is compensated for by the tensioning assembly 1644, which maintains the heating element 1608 in tension, so that the heating element 1608 remains generally concentric and parallel to the central longitudinal axis of the body 1602 or the reactor tube 1632.

The technique described for FIG. 8 for mounting or attaching the heating element 1608 using the top and bottom electrodes 1642 and 1646 and the tensioning assembly 1644 is an alternative embodiment that can be applied to the overall embodiment shown in FIG. 7, given appropriate modifications to support this alternative structure. On the other hand, the technique described for FIG. 7 for mounting or attaching the heating element 1508 using the top and bottom electrodes 1546 and 1548 and the spring bias assembly 1550 is an alternative embodiment that can be applied to the overall embodiment shown in FIG. 8, given appropriate modifications to support this alternative structure.

An interior surface of a wall of the reactor tube 1632 defines an inner volume, all or part of which includes a longitudinal elongated reaction zone generated in the vicinity of the heating element 1608 during gas processing or thermal cracking operations. The reactor tube 1632 is thus the heating or reaction chamber of the thermal cracking apparatus 1600, and the central longitudinal axis of the body 1602 or the reactor tube 1632 is also considered to be a central longitudinal axis of the longitudinal elongated reaction zone.

Electrical power is provided to the heating element 1608 through the top electrode assembly 1642 and the bottom electrode assembly 1646 during gas processing operations. The top electrode assembly 1642 electrically connects to, or near, the top of the heating element 1608. The bottom electrode assembly 1646 electrically connects to, or near, the bottom of the heating element 1608.

The feedstock process gas inlet 1612 is fluidly connected to a feedstock process gas source (not shown). The feedstock process gas inlet 1612 is also attached or mounted to the shells 1628 and 1630 to be in fluid communication with the inner volume of the reactor tube 1632 via apertures or holes through the shells 1628 and 1630, the top plug 1636, and the reactor tube 1632. During gas processing operations, the feedstock process gas is flowed from the source through the feedstock process gas inlet 1612 and into the inner volume (the reaction zone) of the reactor tube 1632 through a series of holes or apertures 1652 in the wall of the reactor tube 1632 near the top of the reactor tube 1632, for embodiments in which the gas flow direction is downward. Within the inner volume or the reaction zone, the feedstock process gas circulates around the heating element 1608, which heats the feedstock process gas in the vicinity thereof to thermally crack the feedstock process gas into constituent elements and/or lower order molecules, i.e., the gaseous and solid products. For embodiments in which the gas flow direction is upward, on the other hand, the feedstock process gas inlet 1612 and the series of holes or apertures 1652 in the wall of the reactor tube 1632 are placed near the bottom of the reactor tube 1632.

In some embodiments, the secondary feedstock process gas inlet 1614 is fluidly connected to a source (not shown) of a second feedstock process gas having additional particles (e.g., nanoparticles) floating therein. The secondary feedstock process gas inlet 1614 is attached or mounted through the shells 1628 and 1630 and the top plug 1636 to be in fluid communication with the inner volume of the reactor tube 1632 via apertures or holes through the shells 1628 and 1630 and the top plug 1636. During gas processing operations, the feedstock process gas with additional particles is flowed from the source through the secondary feedstock process gas inlet 1614 into the inner volume of the reactor tube 1632, i.e., the reaction zone. Within the inner volume or the reaction zone, the feedstock process gas with additional particles mixes with the feedstock process gas from the feedstock process gas inlet 1612. The additional particles (e.g., nanoparticles of Silicon, silicon carbide, etc.) assist in the heating, and thus the thermal cracking, of the feedstock process gas in the reaction zone. In some embodiments, the feedstock process has having additional particles and the secondary feedstock process gas inlet 1614 are considered optional or are not included in the thermal cracking apparatus 1500.

The technique described for FIG. 8 for providing the feedstock process gas with additional particles through the secondary feedstock process gas inlet 1614 is an alternative embodiment that can be applied to the overall embodiment shown in FIG. 7, given appropriate modifications to support this alternative structure. On the other hand, the technique described for FIG. 7 for providing the feedstock process gas with additional particles through the secondary feedstock process gas inlet 1514 is an alternative embodiment that can be applied to the overall embodiment shown in FIG. 8, given appropriate modifications to support this alternative structure.

In some embodiments, the cooling gas inlet and outlet 1616 and 1618 are attached or mounted to the shells 1628 and 1630 to be in fluid communication with the gas coolant region, i.e., the space 1640 between the reactor tube 1632 and the secondary shell 1630, via apertures or holes through the shells 1628 and 1630. During gas processing operations, a coolant gas (e.g., air, nitrogen, a noble gas, etc.) is flowed from a source thereof, through the cooling gas inlet 1616, and into the gas coolant region (space 1640). The coolant gas thus circulates within the gas coolant region, absorbs some of the heat from the reactor tube 1632 (thereby serving to cool the reactor tube 1632), and exits through the outlet 1618 to be cooled, recycled, discarded or stored.

In some other embodiments, the space 1640 between the reactor tube 1632 and the secondary shell 1630 is filled with a thermally insulating or conducting material, rather than having a coolant gas flow therein. In various embodiments, the use or selection of the coolant gas or the thermally insulating or conducting material for the space 1640 generally depends on the thermal requirements for the overall configuration of the thermal cracking apparatus 1600, the type of the feedstock process gas, the type or characteristics of the desired solid and/or gaseous products, and/or the process parameters of the gas processing operations. Different embodiments, in other words, generally have different thermal requirements.

In some embodiments, the cooling fluid inlet and outlet 1620 and 1622 are attached or mounted to the outer shell 1628 to be in fluid communication with the cooling fluid region, i.e., the space 1634 between the shells 1628 and 1630, via apertures or holes through the outer shell 1628. During gas processing operations, a coolant fluid (e.g., water, etc.) is flowed from a source thereof, through the cooling fluid inlet 1620, and into the cooling fluid region (space 1634). The coolant fluid thus circulates within the cooling fluid region, absorbs some of the heat from the secondary shell 1630 (thereby cooling the secondary shell 1630), and exits through the outlet 1622 to be cooled, recycled, discarded or stored. In this manner, the action of the coolant fluid, or the combined action of the coolant fluid and the coolant gas, ensures that the outer surface of the thermal cracking apparatus 1600 (i.e., of the body 1602 or the outer shell 1628) remains cool, or does not become too hot to pose a danger to nearby equipment or personnel.

In the illustrated embodiment, the thermal cracking apparatus 1600 further includes a primary hopper 1656 and a secondary hopper 1658. (As mentioned above for the hopper 1562, in some embodiments, different hoppers 1656 and/or 1658 are used for different applications, so the thermal cracking apparatus 1600 is designed with an attachment mechanism for removal and replacement of the hopper 1656 and/or 1658, so that a clean or different hopper 1656 and/or 1658 can be attached for each application.) The primary hopper 1656 is mounted or attached to the lower portion 1648 of the bottom cap assembly 1606. The primary hopper 1656 generally has lower and upper portions 1660 and 1662 and lower and upper filters 1664 and 1666. The lower portion 1648 of the bottom cap assembly 1606 extends through the upper portion 1662 and the upper filter 1666 down to the lower portion 1660 to provide a fluid connection between the inner volume of the reactor tube 1632 and the lower portion 1660. The upper filter 1666 generally separates the lower and upper portions 1660 and 1662. The lower filter 1664 is disposed at or near the bottom of the lower portion 1660 at the solid product outlet 1626. The solid product outlet 1626 is mounted or attached to the lower portion 1660, at or near a bottom thereof. The gaseous product outlet 1624 is mounted or attached to the upper portion 1662 (at or near a side thereof) to provide a fluid connection between the upper portion 1662 and the secondary hopper 1658.

During gas processing operations, the gaseous and solid products fall or flow down from the inner volume of the reactor tube 1632, through the hole in the flange 1650, through the lower portion 1648 of the bottom cap assembly 1606, and into the lower portion 1660 of the primary hopper 1656, for embodiments in which the gas flow direction is downward. The solid products generally continue to fall and pass out through the solid product outlet 1626. The desired solid product is typically the carbon nano-particles described above; however, some larger aggregate particles, debris or flake material can also sometimes form within the reactor tube 1632 and fall down into the primary hopper 1656. The lower filter 1664 is generally designed or selected to be capable of catching these larger particles and allowing the desired solid product to pass through to the solid product outlet 1626. The larger particles are periodically removed from the primary hopper 1656. For embodiments in which the gas flow direction is upward, on the other hand, the solid products flow out of the reactor tube 1632 near the top thereof, unless the solid products are heavy enough to fall against the gas flow, in which case the solid product outlet can be placed near the bottom of the reactor tube 1632, similar to that described previously.

For embodiments in which the gas flow direction is downward, the gaseous product is generally forced to flow (in the direction of arrows 1668) down from the reactor tube 1632, into the lower portion 1660 of the primary hopper 1656, up through the upper filter 1666, into the upper portion 1662, and out through the gaseous product outlet 1624. (For embodiments in which the gas flow direction is upward, on the other hand, the gaseous product is generally forced to flow out of the reactor tube 1632 near the top thereof.) Some of the solid product (such as the smaller particles) can potentially be swept up in the flow of the gaseous product, instead of falling to the bottom of the primary hopper 1656 as mentioned above. The upper filter 1666 is generally designed or selected to be capable of catching these particles, which eventually are removed with the other solid products through the solid product outlet 1626. An ultrasonic port 1670 (mounted or attached to the upper portion 1662) provides an ultrasonic or mechanical vibrational assist for removing these particles by the upper filter 1666. The gaseous product is exhausted with a Venturi assist and a flow of nitrogen gas through the gaseous product outlet 1624 to the secondary hopper 1658. Most of the solid product has been removed from the gaseous product at this point, but some can still remain. Thus, additional gas/solid separation via cyclone or electrical precipitation is implemented for further separation at the secondary hopper 1658. The gaseous products are then removed by flowing through a gaseous product outlet 1672 from the secondary hopper 1658. The gaseous product outlet 1672 is mounted or attached to the secondary hopper 1658 to provide a fluid connection to the interior of the hopper 1658. The gaseous product outlet 1672 is also fluidly connected to a downstream storage apparatus or further gas processing apparatus. The gaseous products are thus flowed out through the gaseous product outlet 1564 to the downstream storage apparatus or further gas processing apparatus.

The exhaust system technique described for FIG. 8 for exhausting and separating the gaseous and solid products through the hoppers 1656 and 1658 is an alternative embodiment that can be applied to the overall embodiment shown in FIG. 7, given appropriate modifications to support this alternative structure. On the other hand, the exhaust system technique described for FIG. 7 for exhausting and separating the gaseous and solid products through the hopper 1562 is an alternative embodiment that can be applied to the overall embodiment shown in FIG. 8, given appropriate modifications to support this alternative structure.

In some situations, some of the solid products can accumulate within the inner volume of the reactor tube 1632, e.g., on the interior surface of the wall of the reactor tube 1632 and/or the heating element 1608. Some embodiments may also use any appropriate structures or subassemblies for forcibly removing the solid products or cleaning the reaction zone.

Reference has been made in detail to embodiments of the disclosed invention, one or more examples of which have been illustrated in the accompanying drawings. Each example has been provided by way of explanation of the present technology, not as a limitation of the present technology. In fact, while the specification has been described in detail with respect to specific embodiments of the invention, it will be appreciated that those skilled in the art, upon attaining an understanding of the foregoing, may readily conceive of alterations to, variations of, and equivalents to these embodiments. For instance, features illustrated or described as part of one embodiment may be used with another embodiment to yield a still further embodiment. Thus, it is intended that the present subject matter covers all such modifications and variations within the scope of the appended claims and their equivalents. These and other modifications and variations to the present invention may be practiced by those of ordinary skill in the art, without departing from the scope of the present invention. Furthermore, those of ordinary skill in the art will appreciate that the foregoing description is by way of example only, and is not intended to limit the invention.

What is claimed is:

1. An apparatus to thermally crack a hydrocarbon as to produce carbon nanoparticles and carbon aggregates, comprising:
   a reaction tube configured to receive the hydrocarbon gas;
   a heating element disposed along a longitudinal axis of reaction tube and within the reaction tube wherein the heating element is held in position by one or more of a spring bias assembly or a pneumatic tensioning assembly; and a pair of cap assemblies configured to engage the ends of the reaction tube wherein the cap assemblies provide one or more of:
an outlet fluidly coupled to the reaction tube to remove the carbon nanoparticles and carbon aggregates generated during thermal cracking; or
at least one opening to enable one or more of the spring bias assembly, the pneumatic tensioning assembly, or a pair of heating element electrodes to connect to the heating element.

2. The apparatus of claim 1, wherein the carbon nanoparticles and carbon aggregates have a ratio of carbon to other elements, except hydrogen, greater than 99.9%.

3. The apparatus of claim 1, wherein the carbon nanoparticles and carbon aggregates are characterized by a first Raman peak at approximately 1350 cm$^{-1}$ and a second Raman peak at approximately 1580 cm$^{-1}$.

4. The apparatus of claim 1, wherein the carbon aggregates comprise one or more multi-walled spherical fullerenes.

5. The apparatus of claim 1, wherein the carbon based aggregates have a dimension approximately between 10 microns and 500 microns.

6. The apparatus of claim 1, wherein the carbon aggregates include one or more graphene-based layers or structures.

7. The apparatus of claim 1, wherein the carbon aggregates have a specific surface area approximately between 10 m$^2$/g and 200 m$^2$/g.

8. The apparatus of claim 1, further comprising a pellet formed by compression of at least some of the plurality of carbon aggregates.

9. The apparatus of claim 1, wherein the reaction tube is configured to receive hydrocarbon gas at a low rate of approximately between 1 slm and 10 slm.

10. The apparatus of claim 1, wherein the heating element is configured to heat the hydrocarbon gas to a cracking temperature of approximately between 1600° C. and 2200° C.

11. The apparatus of claim 1, further comprising one or more hoppers fluidly connected to the outlet.

12. The apparatus of claim 11, wherein the one or more hoppers comprise one or more filters.

13. An apparatus to thermally crack a hydrocarbon feedstock gas, comprising:
a first reactor tube including a reaction zone;
a second reactor tube disposed concentrically with and outside the first reactor tube;
a feedstock gas preheating region disposed between the first and second reactor tubes, wherein the preheating region is in fluid communication with the reaction zone;
a heating element disposed within the reaction zone and along a longitudinal axis of the reaction zone and held in position using one or more of a spring bias assembly or a pneumatic tensioning assembly; and
one or more shells disposed concentrically with each other and outside the second reactor tube, wherein the one or more shells define one or more cooling fluid regions between the one or more shells and the second reactor tube, and wherein the feedstock gas is thermally cracked in the reaction zone to produce carbon nanoparticles and carbon aggregates.

14. The apparatus of claim 13, wherein the first reactor tube is made of at least one of quartz and alumina.

15. The apparatus of claim 13, wherein the second reactor tube is made of at least one of steel and titanium.

16. The apparatus of claim 13, wherein the first reactor tube further comprises a plurality of gas distribution apertures disposed along the circumference of the tube, and wherein the feedstock gas from the preheating region is distributed into the reaction zone through the apertures.

17. The apparatus of claim 13, wherein the first reactor tube further comprises a secondary gas inlet for feeding to the reaction zone a secondary gas having nanoparticles of high temperature materials to coat the nanoparticles with carbon produced during the cracking of the feedstock gas.

18. The apparatus of claim 17, wherein the nanoparticles comprise one or more of silicon or silicon carbide.

19. The apparatus of claim 13, wherein the one or more cooling fluid regions is filled with insulating material.

* * * * *